(12) United States Patent
Tao et al.

(10) Patent No.: US 11,198,897 B2
(45) Date of Patent: Dec. 14, 2021

(54) RAPID ANTIBIOTIC SUSCEPTIBILITY TESTING BY TRACKING SUB-MICRON SCALE MOTION OF SINGLE BACTERIAL CELLS

(71) Applicant: Arizona Board of Regents on behalf of Arizona State University, Scottsdale, AZ (US)

(72) Inventors: Nongjian Tao, Fountain Hills, AZ (US); Karan Syal, Jalandhar (IN)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 17/072,742

(22) Filed: Oct. 16, 2020

(65) Prior Publication Data

US 2021/0054432 A1    Feb. 25, 2021

Related U.S. Application Data

(63) Continuation of application No. 16/633,812, filed as application No. PCT/US2018/043638 on Jul. 25, 2018, now Pat. No. 10,947,576.

(Continued)

(51) Int. Cl.
*G06K 9/00* (2006.01)
*C12Q 1/18* (2006.01)
(Continued)

(52) U.S. Cl.
CPC ............... *C12Q 1/18* (2013.01); *G01N 15/14* (2013.01); *G01N 33/54313* (2013.01); *G06K 9/0014* (2013.01); *G01N 2015/0065* (2013.01)

(58) Field of Classification Search
CPC .... C12Q 1/18; G01N 15/14; G01N 33/54313; G01N 33/56911; G01N 2015/0065;
(Continued)

(56) References Cited

U.S. PATENT DOCUMENTS 3,832,532 A    8/1974   Praglin et al.
5,985,891 A    11/1999  Rowe
(Continued)

FOREIGN PATENT DOCUMENTS

EP    2821499 A1    2/2017
EP    2757371 A1    9/2017
(Continued)

OTHER PUBLICATIONS

Grant, C. et al., "Optimization of Immobilized Bacterial Disaccharides for Surface Plasmon Resonance Imaging Measurements of Antibody Binding", Langmuir, Nov. 2008, vol. 24, No. 24, pp. 14125-14132 <DOI:10.1021/la8026489>.

(Continued)

*Primary Examiner* — Atiba O Fitzpatrick
(74) *Attorney, Agent, or Firm* — Withrow & Terranova, P.L.L.C.

(57) ABSTRACT

A method for rapid antibiotic susceptibility testing by tracking sub-micron scale motion of single bacterial cells including obtaining a biological sample from a subject including live bacteria. Different doses of antibiotic are added to a multi-well glass slide and adding portions of the biological sample to the wells. Bacterial cells are tethered onto the surface. The tethered bacterial cells are imaged and tracked. Bacterial sub-micron motion of tethered cells is measured at the different doses. A processor performs statistical analysis on a population of cells for each antibiotic dose to generate an antibiotic dose curve proportional to the motion changes, where the antibiotic dose curve plots data including a (Continued)

decrease in movement over time indicating a proportional effectiveness of an antibiotic applied to a well.

20 Claims, 22 Drawing Sheets

Related U.S. Application Data

(60) Provisional application No. 62/536,895, filed on Jul. 25, 2017.

(51) Int. Cl.
*G01N 15/14* (2006.01)
*G01N 33/543* (2006.01)
*G01N 15/00* (2006.01)

(58) Field of Classification Search
CPC .............. G06K 9/0014; G06T 7/246; G06T 2207/10016; G06T 2207/10056; G06T 2207/30024
See application file for complete search history.

(56) References Cited

U.S. PATENT DOCUMENTS

| | | | |
|---|---|---|---|
| 6,153,400 A | 11/2000 | Matsumura et al. | |
| 6,224,891 B1 | 5/2001 | Rafter | |
| 6,303,572 B1 | 10/2001 | Rowe | |
| 6,849,422 B1 | 2/2005 | Wiles et al. | |
| 7,011,826 B1 | 3/2006 | Rowe | |
| 7,132,837 B1 | 11/2006 | Tao | |
| 7,341,841 B2 | 3/2008 | Metzger et al. | |
| 7,582,415 B2 | 9/2009 | Straus | |
| 7,763,426 B2 | 7/2010 | Haake et al. | |
| 7,785,001 B2 | 8/2010 | Tao et al. | |
| 8,021,848 B2 | 9/2011 | Straus | |
| 8,071,319 B2 | 12/2011 | Metzger et al. | |
| 8,416,417 B2 | 4/2013 | Foley et al. | |
| 8,460,887 B2 | 6/2013 | Goldberg et al. | |
| 8,465,634 B2 | 6/2013 | Tao et al. | |
| 8,545,683 B2 | 10/2013 | Tao et al. | |
| 8,637,233 B2 | 1/2014 | Nickel et al. | |
| 8,785,148 B2 | 7/2014 | Sauer-Budge et al. | |
| 8,926,822 B2 | 1/2015 | Tao et al. | |
| 9,133,498 B2 | 9/2015 | Kwon et al. | |
| 9,677,109 B2 | 6/2017 | Shamsheyeva et al. | |
| 9,772,305 B2 | 9/2017 | Tao | |
| 9,909,993 B2 | 3/2018 | Tao et al. | |
| 9,915,813 B2 | 3/2018 | Olesen et al. | |
| 10,078,074 B2 | 9/2018 | Tsow et al. | |
| 10,078,795 B2 | 9/2018 | Tao et al. | |
| 10,143,401 B2 | 12/2018 | Tao et al. | |
| 10,222,372 B2 | 3/2019 | Tao et al. | |
| 10,266,867 B2 | 4/2019 | Son et al. | |
| 10,401,298 B2 | 9/2019 | Tao et al. | |
| 10,408,757 B2 | 9/2019 | Tao et al. | |
| 10,413,226 B2 | 9/2019 | Tao et al. | |
| 10,539,530 B2 | 1/2020 | Tao | |
| 10,947,576 B2 | 3/2021 | Tao et al. | |
| 2007/0264717 A1 | 11/2007 | Montijn | |
| 2009/0053188 A1 | 2/2009 | Rowe | |
| 2009/0226521 A1* | 9/2009 | Smyth ................ | A61K 47/6921 424/484 |
| 2009/0315987 A1* | 12/2009 | Straus ................ | G01N 21/6428 348/79 |
| 2012/0244519 A1 | 9/2012 | Olesen et al. | |
| 2012/0270330 A1 | 10/2012 | Tao et al. | |
| 2013/0089476 A1* | 4/2013 | Weichselbaum ... | G01N 33/4875 422/554 |
| 2013/0115137 A1 | 5/2013 | Tao et al. | |
| 2013/0196364 A1 | 8/2013 | Kwon et al. | |
| 2014/0276104 A1 | 9/2014 | Tao et al. | |
| 2014/0278136 A1 | 9/2014 | Shamsheyeva et al. | |
| 2014/0287403 A1 | 9/2014 | Kasas et al. | |
| 2017/0218426 A1* | 8/2017 | Shamsheyeva .......... | C12Q 1/02 |
| 2018/0140255 A1 | 5/2018 | Tao et al. | |
| 2018/0274020 A1* | 9/2018 | Ismagilov ............ | C12Q 1/6809 |
| 2019/0082972 A1 | 3/2019 | Tao et al. | |
| 2019/0170748 A1 | 6/2019 | Tao et al. | |
| 2019/0239761 A1 | 8/2019 | Tao et al. | |
| 2019/0325257 A1 | 10/2019 | Tao et al. | |
| 2020/0000370 A1 | 1/2020 | Tao et al. | |
| 2020/0022628 A1 | 1/2020 | Tao et al. | |
| 2020/0096472 A1 | 3/2020 | Tao et al. | |
| 2020/0156074 A1 | 5/2020 | Tao et al. | |

FOREIGN PATENT DOCUMENTS

| | | |
|---|---|---|
| WO | 2008021614 A2 | 2/2008 |
| WO | 2008148025 A1 | 12/2008 |
| WO | 2009064985 A1 | 5/2009 |
| WO | 2009132262 A1 | 10/2009 |
| WO | 2010030874 A1 | 3/2010 |
| WO | 2010036940 A2 | 4/2010 |
| WO | 2010048511 A1 | 4/2010 |
| WO | 2011031500 A2 | 3/2011 |
| WO | 2011140239 A2 | 11/2011 |
| WO | 2013019843 A2 | 2/2013 |
| WO | 2014116604 A1 | 7/2014 |
| WO | 2015103459 A1 | 7/2015 |
| WO | 2016207065 A1 | 12/2016 |
| WO | 2017156084 A2 | 9/2017 |
| WO | 2018022567 A1 | 2/2018 |
| WO | 2018057753 A1 | 3/2018 |
| WO | 2018170009 A1 | 9/2018 |
| WO | 2018187548 A2 | 10/2018 |
| WO | 2018213790 A2 | 11/2018 |
| WO | 2018213790 A8 | 11/2018 |
| WO | 2019050847 A1 | 3/2019 |

OTHER PUBLICATIONS

Hancock, R.,"The End of an Era?", Nature Review Drug Discovery, Dec. 2006, vol. 6, pp. 28-28 <DOI:10.1038/nrd2223>.

Hayden, R. et al., "Rapid Antimicrobial Susceptibility Testing Using Forward Laser Light Scatter Technology", Journal of Clinical Microbiology, Nov. 2016 [available online Aug. 2016], vol. 54, pp. 2701-2706 <DOI:10.1128/JCM.01475-16>.

Hirst, D. et al., "Combined Mass and Structural Kinetic Analysis of Multistate Antimicrobial Peptide-Membrane Interactions", Analytical Chemistry, Sep. 2013, vol. 85, No. 19, pp. 9296-9304 <DOI:10.1021/ac402148v >.

Holden, M. et al., "Direct Transfer of Membrane Proteins from Bacteria to Planar Bilayers for Rapid Screening by Single-Channel Recording", Nature Chemical Biology, Jun. 2006 [available online May 2006], vol. 2, pp. 314-318 <DOI:10.1038/nchembio793>.

Howell, M. et al., "Application of a Microcalorimetric Method for Determining Drug Susceptibility in Mycobacterium Species", Journal of Clinical Microbiology, Jan. 2012 [available online Nov. 2011], vol. 50, pp. 16-20 <DOI:10.1128/JCM.05556-11>.

Huang, B. et al., "Surface Plasmon Resonance Imaging Using a High Numerical Aperture Microscope Objective", Analytical Chemistry, Apr. 2007 [available online Feb. 2007], vol. 79, No. 7, pp. 2979-2983 <DOI:10.1021/ac062284x>.

Humphries, R. et al., "Emerging Resistance, New Antimicrobial Agents . . . but No Tests! The Challenge of Antimicrobial Susceptibility Testing in the Current US Regulatory Landscape", Clinical Infectious Diseases, Jul. 2016 [available online Mar. 2016], vol. 63, No. 1, pp. 83-88 <DOI:10.1093/cid/ciw201>.

Ivancic, V. et al., "Rapid Antimicrobial Susceptibility Determination of Uropathogens in Clinical Urine Specimens by Use of ATP Bioluminescence", Journal of Clinical Microbiology, Apr. 2008, vol. 46, No. 4, pp. 1213-1219 <DOI:10.1128/JCM.02036-07>.

Jepras, R. et al., "Rapid Assessment of Antibiotic Effects on *Escherichia coli* by Bis-( 1,3-Dibutylbarbituric Acid) Trimethine Oxonol and Flow Cytometry", Antimicrobial Agents and Chemotherapy, Sep. 1997, vol. 41, No. 9, pp. 2001-2005 <DOI:10.1128/AAC.41.9.2001>.

(56) References Cited

OTHER PUBLICATIONS

Jorgensen, J. et al., "Antimicrobial Susceptibility Testing: A Review of General Principles and Contemporary Practices", Clinical Infectious Diseases, Dec. 2009, vol. 49, No. 11, pp. 1749-1755 <DOI:10.1086/647952>.
Kadlec, M. et al., "A Cell Phone-Based Microphotometric System for Rapid Antimicrobial Susceptibility Testing", Journal of Laboratory Automation, Jun. 2014 [available online May 2013], vol. 19, No. 3, pp. 258-266 <DOI: 10.1177/2211068213491095>.
Kasas, S. et al., "Detecting Nanoscale Vibrations as Signature of Life", Proceedings of the National Academy of Sciences of the United States of America, Jan. 2015 [available online Dec. 2014], vol. 112, No. 2, pp. 378-381 <DOI: 10.1073/pnas.1415348112>.
Kearns, D., "A Field Guide to Bacterial Swarming Motility", Nature Reviews Microbiology, Aug. 2010, vol. 8, pp. 634-644 <DOI:10.1038/nrmicro2405>.
Kim, S. et al., "Miniaturized Antimicrobial Susceptibility Test by Combining Concentration Gradient Generation and Rapid Cell Culturing", Antibiotics, Dec. 2015 [available online Oct. 2015], vol. 4, No. 4, pp. 455-466 <DOI: 10.3390/antibiotics4040455>.
Kim, Y., "Diffusivity of Bacteria", Korean Journal of Chemical Engineering, 1996, vol. 13, pp. 282-287 <DOI:10.1007/BF02705951>.
King, A., "Recommendations for susceptibility tests on fastidious organisms and those requiring special handling", The Journal of Antimicrobial Chemotherapy, Jul. 2001, vol. 48, pp. 77-80 <DOI: 10.1093/jac/48.suppl_1.77>.
Kinnunen, P. et al., "Monitoring the Growth and Drug Susceptibility of Individual Bacteria Using Asynchronous Magnetic Bead Rotation Sensors", Biosensors & Bioelectronics, Jan. 2011 [available online Oct. 2014], vol. 26, No. 5, pp. 2751-2755 <DOI:10.1016/j.bios.2010.10.010>.
Kinnunen, P. et al., "Self-Assembled Magnetic Bead Biosensor for Measuring Bacterial Growth and Antimicrobial Susceptibility Testing", Small, Aug. 2012 [available online Jun. 2012], vol. 8, No. 16, pp. 2477-2482 <DOI:10.1002/smll.201200110>.
Kumar, A. et al., "Duration of Hypotension before Initiation of Effective Antimicrobial Therapy Is the Critical Determinant of Survival in Human Septic Shock", Critical Care Medicine, Jun. 2006, vol. 34, No. 6, pp. 1589-1596 <DOI:10.1097/01.CCM.0000217961.75225.E9>.
Kwa, A. et al., "Polymyxin B: Similarities to and Differences from Colistin (Polymyxin E)", Expert Review of Anti-Infective Therapy, Oct. 2007, vol. 5, No. 5, pp. 811-821 <DOI:10.1586/14787210.5.5.811>.
Laxminarayan, R. et al., "Antibiotic Resistance—the Need for Global Solutions", The Lancet Infectious Diseases, Nov. 2013, vol. 13, pp. 1057-1098 <DOI:10.1016/S1473-3099(13)70318-9>.
Lee, A., "How Lipids Affect the Activities of Integral Membrane Proteins", Biochimica et Biophysica Acta, Nov. 2004, [available online Jul. 2004] vol. 1666, pp. 62-87 <DOI: 10.1016/j.bbamem.2004.05.012>.
Lidstrom, M. et al., "The Role of Physiological Heterogeneity in Microbial Population Behavior", Nature Chemical Biology, Oct. 2010 [available online Sep. 2010], vol. 6, No. 10, pp. 705-712 <DOI:10.1038/nchembio.436>.
Lim, L. et al., "Resurgence of Colistin: A Review of Resistance, Toxicity, Pharmacodynamics, and Dosing", Pharmacotherapy, Dec. 2010, vol. 30, No. 12, pp. 1279-1291 <DOI:10.1592/phco.30.12.1279>.
Lissandrello, C. et al., "Nanomechanical Motion of *Escherichia coli* Adhered to a Surface", Applied Physics Letters, Sep. 2014, vol. 105, No. 11, pp. 113701-113704 <DOI:10.1063/1.4895132>.
Liu, J. et al., "Metabolic Co-Dependence Gives Rise to Collective Oscillations within Biofilms", Nature, Jul. 2015, vol. 623, pp. 550-554 <DOI:10.1038/nature14660>.
Liu, Q. et al., "Liposomes in Biosensors", Analyst, Jan. 2013 [available online Sep. 2012], vol. 138, No. 2, pp. 391-409 <DOI:10.1039/C2AN36140J>.
Liu, Y. et al., "Emergence of Plasmid-Mediated Colistin Resistance Mechanism MCR-1 in Animals and Human Beings in China: A Microbiological and Molecular Biological Study", The Lancet Infectious Diseases, Feb. 2016 [available online Nov. 2015], vol. 16, No. 10, pp. 161-168 <DOI:10.1016/S1473-3099(15)00424-7>.
Longo, G. et al., "Rapid Detection of Bacterial Resistance to Antibiotics Using AFM Cantilevers as Nanomechanical Sensors", Nature Nanotechnology, Jun. 2013, vol. 8, pp. 522-526 <DOI:10.1038/nnano.2013.120>.
Lower, S. et al., "Polymorphisms in Fibronectin Binding Protein A of *Staphylococcus aureus* Are Associated with Infection of Cardiovascular Devices", Proceedings of the National Academy of Sciences of the United States of America, Nov. 2011 [available online Oct. 2011], vol. 108, p. 18372-18377 <DOI:10.1073/pnas.1109071108>.
Lu, Y. et al., "Single Cell Antimicrobial Susceptibility Testing by Confined Microchannels and Electrokinetic Loading", Analytical Chemistry, Apr. 2013 [available online Feb. 2013], vol. 85, No. 8, pp. 3971-3976 <DOI:10.1021/ac4004248>.
Mach, K. et al., "A Biosensor Platform for Rapid Antimicrobial Susceptibility Testing Directly from Clinical Samples", The Journal of Urology, Jan. 2011 [available online Nov. 2010], vol. 185, No. 1, pp. 148-153 <DOI:10.1016/j.juro.2010.09.022>.
Mann, T. et al., "Antibiotic Susceptibility Testing at a Screen-Printed Carbon Electrode Array", Analytical Chemistry, Jan. 2008, vol. 80, No. 3, pp. 843-848 <DOI:10.1021/ac701829c>.
Martineau, F. et al., "Correlation between the Resistance Genotype Determined by Multiplex PCR Assays and the Antibiotic Susceptibility Patterns of *Staphylococcus aureus* and *Staphylococcus epidermidis*", Antimicrobial Agents and Chemotherapy, Feb. 2000, vol. 44, No. 2, pp. 231-238 <DOI:10.1128/aac.44.2.231-238.2000>.
Martinez, J. et al., "What Is a Resistance Gene ? Ranking Risk in Resistomes", Nature Reviews Microbiology, Dec. 2014, vol. 13, No. 2, pp. 116-123 <DOI:10.1038/nrmicro3399>.
McGann, P. et al., "*Escherichia coli* Harboring Mcr-1 and Bia CTX-M on a Novel IncF Plasmid: First Report of Mcr-1 in the United States", Antimicrobial Agents and Chemotherapy, Jul. 2016 [available online May 2016], vol. 60, No. 7, pp. 4420-4421 <DOI:10.1128/AAC.01103-16>.
McGregor, A. et al., "The MicroScan WalkAway Diagnostic Microbiology System—an Evaluation", Pathology, Apr. 1995, vol. 27, No. 2, pp. 172-176 <DOI:10.1080/00313029500169822>.
Medina, M. et al., "Real-Time Analysis of Antibody Binding Interactions with Immobilized *E . coli* O157 : H7 Cells Using the BIAcore", Biotechnology Techniques, Feb. 1997, vol. 11, No. 3, pp. 173-176 <DOI:10.1023/a:1018453530459>.
Meizger, S. et al., "Rapid Simultaneous Identification and Quantitation of *Staphylococcus aureus* and Pseudomonas Aeruginosa Directly fromBronchoalveolar Lavage Specimens Using Automated Microscopy", Diagnostic Microbiology and Infectious Disease, Jun. 2014 [available online Dec. 2013], vol. 79, No. 2, pp. 160-165 <DOI:10.1016/j.diagmicrobio.2013.11.029>.
Mohan, R. et al., "A Microfluidic Approach to Study the Effect of Bacterial Interactions on Antimicrobial Susceptibility in Polymicrobial Cultures", RSC Advances, Apr. 2015, vol. 5, pp. 35211-35223 <DOI:10.1039/C5RA04092B>.
Mohan, R. et al., "A Multiplexed Microfluidic Platform for Rapid Antibiotic Susceptibility Testing", Biosensors & Bioelectronics, Nov. 2013 [available online May 2013], vol. 49, pp. 118-125 <DOI:10.1016/j.bios.2013.04.046>.
Mohan, R. et al., "Clinical Validation of Integrated Nucleic Acid and Protein Detection on an Electrochemical Biosensor Array for Urinary Tract Infection Diagnosis", PLoS One, Oct. 2011, vol. 6, No. 10, pp. e26846 <DOI:10.1371/journal.pone.0026846>.
Molaei, M. et al., "Failed Escape: Solid Surfaces Prevent Tumbling of *Escherichia coli*", Physical Review Letters, Aug. 2014, vol. 113, pp. 1-6 <DOI:10.1103/PhysRevLett.113.068103>.
No Author Name, "Roche Gobbles Smarticles", Nature Biotechnology, Oct. 2015, vol. 33, No. 10, pp. 1012-1012 <DOI: 10.1038/nbt1015-1012a>.
Ocampo, P. et al., "Antagonism between Bacteriostatic and Bactericidal Antibiotics Is Prevalent", Antimicrobial Agents Chemo-

(56) References Cited

OTHER PUBLICATIONS therapy, Aug. 2014 [available online Jul. 2014], vol. 58, No. 8, pp. 4573-4582 <DOI:10.1128/AAC.02463-14>.
Park, C. et al., "Isolation of a Nonpathogenic Strain of Citrobacter Sedlakii Which Expresses *Escherichia coli* O157 Antigen", Journal of Clinical Microbiology, May 1998, vol. 36, No. 5, pp. 1408-1409 <DOI:10.1128/JCM.36.5.1408-1409.1998>.
Park, T. et al., "Lab on a Chip Smartphone Quantifies Salmonella from Paper", Lab on a Chip, Dec. 2013 [available online Oct. 2013], vol. 13, No. 24, pp. 4832-4840 <DOI:10.1039/c3lc50976a>.
Parry, B. et al., "The Bacterial Cytoplasm Has Glass-like Properties and Is Fluidized by Metabolic Activity", Cell, Jan. 2014 [available online Dec. 2013], vol. 156, pp. 183-194 <DOI:10.1016/j.cell.2013.11.028>.
Patent Cooperation Treaty, International Searching Authority, International Preliminary Report on Patentability and Written Opinion for PCT/US2018/043638, 7 pages, dated Jan. 28, 2020.
Patent Cooperation Treaty, International Searching Authority, International Search Report for PCT/US2018/043638, 2 pages, dated Nov. 9, 2018.
Pitt, W. et al., "Rapid Separation of Bacteria from Blood—Review and Outlook", Biotechnology Progress, Jul. 2016 [available online Jun. 2016], vol. 32, No. 4, pp. 823-839 <DOI:10.1002/btpr.2299>.
Price, C. et al., "Rapid Antibiotic Susceptibility Phenotypic Characterization of *Staphylococcus aureus* Using Automated Microscopy of Small Numbers of Cells", Journal of Microbiological Methods, Mar. 2014 [available online Jan. 2014], vol. 98, pp. 50-58 <DOI:10.1016/j.mimet.2013.12.021>.
Quach, D. et al., "Bacterial Cytological Profiling (BCP) as a Rapid and Accurate Antimicrobial Susceptibility Testing Method for *Staphylococcus aureus*", EBioMedicine, Jan. 2016, vol. 4, pp. 95-103 <DOI:10.1016/j.ebiom.2016.01.020>.
Reyes, R. et al., "Mechanisms of O-Antigen Structural Variation of Bacterial Lipopolysaccharide ( LPS )", in The Complex World of Polysaccharides, Chapter 3, Oct. 2012, 28 pages <DOI:10.5772/48147>.
Rogers, G. et al., "The Exclusion of Dead Bacterial Cells Is Essential for Accurate Molecular Analysis of Clinical Samples", Clinical Microbiology and Infection, Nov. 2010, vol. 16, No. 11, pp. 1656-1658 <DOI:10.1111/i.1469-0691.2010.03189.x>.
Rolain, J. et al., "Real-Time PCR for Universal Antibiotic Susceptibility Testing", Journal of Antimicrobial Chemotherapy, Aug. 2004 [available online Jul. 2004], vol. 54, No. 2, pp. 538-541 <DOI:10.1093/jac/dkh324>.
Saylor, C. et al., "Monoclonal Antibody-Based Therapies for Microbial Diseases", Vaccine, Dec. 2009, vol. 27, No. 6, pp. G38-G46 <DOI:10.1016/j.vaccine.2009.09.105>.
Schoepp, N. et al., "Digital Quantification of DNA Replication and Chromosome Segregation Enables Determination of Antimicrobial Susceptibility after Only 15 Minutes of Antibiotic Exposure Zuschriften", Angewandte Chemie (International Edition in English), Aug. 2016 [available online Jun. 2016], vol. 55, No. 33, pp. 9709-9713 <DOI:10.1002/anie.201602763>.
Shan, X. et al., "Detection of Charges and Molecules with Self-Assembled Nano-Oscillators", Nano Letters, Jun. 2014, vol. 14, No. 7, pp. 4151-4157 <DOI:10.1021/nl501805e>.
Shan, X. et al., "Imaging the Electrocatalytic Activity of Single Nanoparticles", Nature Nanotechnology, Oct. 2012, vol. 7, No. 10, pp. 668-672 <DOI:10.1038/nnano.2012.134>.
Shen, S. et al., "Note: An Automated Image Analysis Method for High-Throughput Classification of Surface-Bound Bacterial Cell Motions", Review of Scientific Instruments, Dec. 2015, vol. 86, pp. 1-4 <DOI:10.1063/1.4937479>.
Shen, Z. et al., "Non-Labeled QCM Biosensor for Bacterial Detection Using Carbohydrate and Lectin Recognitions", Analytical Chemistry, Feb. 2007, vol. 79, pp. 2312-2319 <DOI:10.1021/ac061986j>.

Sheng, J. et al., "Digital Holographic Microscope for Measuring Three-Dimensional Particle Distributions and Motions", Applied Optics, 2006, vol. 45, No. 16, pp. 3893-3901 <DOI:10.1364/AO.45.003893>.
Sin, M. et al., "Advances and Challenges in Biosensor-Based Diagnosis of Infectious Diseases", Expert Review of Molecular Diagnostics, Mar. 2014 [available online Feb. 2014], vol. 14, No. 2, pp. 225-244 <DOI:10.1586/14737159.2014.888313>.
Sinn, I. et al., "Asynchronous Magnetic Bead Rotation Microviscometer for Rapid, Sensitive, and Label-Free Studies of Bacterial Growth and Drug Sensitivity", Analytical Chemistry, Jun. 2012 [available online Apr. 2012], vol. 84, No. 12, pp. 5250-5256 <DOI:10.1021/ac300128p>.
Sivanandan, S. et al., "Choice and Duration of Antimicrobial Therapy for Neonatal Sepsis and Meningitis", International Journal of Pediatrics, Nov. 2011, vol. 2011, pp. 1-9 <DOI: 10.1155/2011/712150>.
Sochacki, K. et al., "Real-Time Attack on Single *Escherichia coli* Cells by the Human Antimicrobial Peptide LL-37", Proceedings of the National Academy of Sciences of the United States of America, Apr. 2011, vol. 108, No. 16, pp. E77-81 <DOI: 10.1073/pnas.1101130108>.
Sokolov, A. et al., "Reduction of Viscosity in Suspension of Swimming Bacteria", Physical Review Letters, Oct. 2009 [available online Sep. 2009], vol. 103, pp. 2-5 <DOI:10.1103/PhysRevLett.103.148101>.
Song, L. et al., "Nanoscopic Vibrations of Bacteria with Different Cell-Wall Properties Adhering to Surfaces under Flow and Static Conditions", ACS Nano, Jul. 2014, vol. 8, No. 8, pp. 8457-8467 <DOI:10.1021/nn5030253>.
Subramanian, A. et al., "A Mixed Self-Assembled Monolayer-Based Surface Plasmon Immunosensor for Detection of *E. coli* O157:H7", Biosensors & Bioelectronics, Jan. 2006 [available online May 2005], vol. 21, No. 7, pp. 998-1006 <DOI: 10.1016/j.bios.2005.03.007>.
Syal, K. et al., "Antimicrobial Susceptibility Test with Plasmonic Imaging and Tracking of Single Bacterial Motions on Nanometer Scale", ACS Nano, Jan. 2016 [available online Dec. 2015], vol. 10, No. 1, pp. 845-852 <DOI:10.1021/acsnano.5b05944>.
Syal, K. et al., "Current and Emerging Techniques for Antibiotic Susceptibility Tests", Theranostics, Apr. 2017, vol. 7, No. 7, pp. 1795-1805 <DOI:10.7150/thno.19217>.
Syal, K. et al., "Plasmonic Imaging of Protein Interactions with Single Bacterial Cells", Biosensors & Bioelectronics, Jan. 2015 [available online Jul. 2014], vol. 63, pp. 131-137 <DOI:10.1016/j.bios.2014.06.069>.
Syal, K. et al., "Rapid Antibiotic Susceptibility Testing of Uropathogenic *E. coli* by Tracking Submicron Scale Motion of Single Bacterial Cells", ACS Sensors, Aug. 2017 [available online Jul. 2017], vol. 2, No. 8, pp. 1231-1239 <DOI:10.1021/acssensors.7b00392>.
Tawil, N. et al., "Surface Plasmon Resonance Detection of *E. coli* and Methicillin-Resistant *S. aureus* Using Bacteriophages", Biosensors & Bioelectronics, Aug.-Sep. 2012, [available online May 2012], vol. 37, pp. 24-29 <DOI:10.1016/j.bios.2012.04.048>.
Torun, O. et al., "Comparison of Sensing Strategies in SPR Biosensor for Rapid and Sensitive Enumeration of Bacteria", Biosensors & Bioelectronics, Aug.-Sep. 2012 [available online May 2012], vol. 37, pp. 53-60 <DOI:10.1016/j.bios.2012.04.034>.
Tracy, B. et al., "Flow Cytometry for Bacteria: Enabling Metabolic Engineering, Synthetic Biology and the Elucidation of Complex Phenotypes", Current Opinions in Biotechnology, Feb. 2010, vol. 21, No. 1, pp. 85-99 <DOI:10.1016/i.copbio.2010.02.006>.
U.S. Appl. No. 16/500,370, Tao et al., filed Oct. 5, 2019.
U.S. Appl. No. 16/613,745, Tao, filed Nov. 14, 2019.
U.S. Appl. No. 16/644,453, Tao et al., filed Mar. 4, 2020.
Van Belkum, A. et al., "Next-Generation Antimicrobial Susceptibility Testing", Journal of Clinical Microbiology, Jul. 2013 [available online Mar. 2013], vol. 51, No. 7, pp. 2018-2024 <DOI:10.1128/JCM.00313-13>.
Van Boeckel, T. et al., "Global Antibiotic Consumption 2000 to 2010: An Analysis of National Pharmaceutical Sales Data", The

(56) References Cited

OTHER PUBLICATIONS

Lancet Infectious Diseases, Aug. 2014 [available online Jul. 2014], vol. 14, No. 8, pp. 742-750 <DOI:10.1016/S1473-3099(14)70780-7>.

Van Der Mei, H. et al., "Bacterial Cell Surface Heterogeneity: A Pathogen's Disguise", PLoS Pathogens, Aug. 2012, vol. 8, pp. e1002821 <DOI:10.1371/journal.ppat.1002821>.

Van Houdt, R. et al., "Role of Bacterial Cell Surface Structures in Escherichia 111 coli Biofilm Formation", Research in Microbiology, Jun.-Jul. 2005 [avaialble online Mar. 2005], vol. 156, pp. 626-633 <DOI:10.1016/j.resmic.2005.02.005>.

Von Ah, U. et al., "Isothermal Micro Calorimetry—a New Method for MIC Determinations: Results for 12 Antibiotics and Reference Strains of E. coli and S. aureus", BMC Microbiology, May 2009, vol. 9, No. 106, 14 pages <DOI:10.1186/1471-2180-9-106>.

Wang, S. et al., "Label-Free Imaging, Detection, and Mass Measurement of Single Viruses by Surface Plasmon Resonance", Proceedings of the National Academy of Sciences of the United States of America, Sep. 2010 [available online Aug. 2010], vol. 107, No. 37, pp. 16028-16032 <DOI:10.1073/pnas.1005264107>.

Wang, W. et al., "Label-Free Measuring and Mapping of Binding Kinetics of Membrane Proteins in Single Living Cells", Nature Chemistry, Oct. 2012 [available online Aug. 2012], vol. 4, No. 12, pp. 846-873 <DOI:10.1038/nchem.1434>.

Wang, W. et al., "Single Cells and Intracellular Processes Studied by a Plasmonic-Based Electrochemical Impedance Microscopy", Nature Chemistry, Mar. 2011 [available online Jan. 2011], vol. 3, No. 3, pp. 249-255 <DOI:10.1038/nchem.961>.

Wang, X. et al., "Fluorescent pH-Sensitive Nanoparticles in an Agarose Matrix for Imaging of Bacterial Growth and Metabolism", Angewandte Chemie International Edition English, Oct. 2012, vol. 52, pp. 406-409 <DOI:10.1002/anie.201205715>.

Wanger, A. et al., "Evaluation of the BD Phoenix System for Identification and Susceptibility Testing of Gram-Positive and Negative Clinical Isolates", White Paper, presented at the 105th General Meeting of the American Society tor Microbiology, 2005, 4 pages.

Waswa, J. et al., "Direct Detection of E. coli O157:H7 in Selected Food Systems by a Surface Plasmon Resonance Biosensor", LWT—Food Science Technology, Mar. 2007 [available online Jan. 2006], vol. 40, No. 2, pp. 187-192 <DOI:10.1016/j.lwt.2005.11.001>.

Whitfield, C. et al., "Stop and Go: Regulation of Chain Length in the Biosynthesis of Bacterial Polysaccharides", Nature Structural and Molecular Biology, Feb. 2008, vol. 15, pp. 121-123 <DOI:10.1038/nsmb0208-121>.

Wiegand, I. et al., "Agar and Broth Dilution Methods to Determine the Minimal Inhibitory Concentration (MIC) of Antimicrobial Substances", Nature Protocols, Jan. 2008, vol. 3, No. 2, pp. 163-175 <DOI:10.1038/nprot.2007.521>.

Winstanley, T. et al., "Expert Systems in Clinical Microbiology", Clinical Microbiology Reviews, Jul. 2011, vol. 24, No. 3, pp. 515-556 <DOI:10.1128/CMR.00061-10>.

Wood, K. et al., "Pharmacoeconomic Implications of New Therapies in Sepsis", Pharmacoeconomics, Feb. 2004, vol. 22, No. 14, pp. 895-906 <DOI:10.2165/00019053-200422140-00001>.

Woodward, R. et al., "In Vitro Bacterial Polysaccharide Biosynthesis: Defining the Functions of Wzy and Wzz", Nature Chemical Biology, Jun. 2010 [available online Apr. 2010], vol. 6, No. 6, pp. 418-423 <DOI:10.1038/nchembio.351>.

Woude, M. et al., "Phase and Antigenic Variation in Bacteria Phase and Antigenic Variation in Bacteria", Clinical Microbiology Reviews, Jul. 2004, vol. 17, No. 3, pp. 581-611 <DOI:10.1128/CMR.17.3.581-611.2004>.

Yang, Y. et al., "Label-Free Tracking of Single Organelle Transportation in Cells with Nanometer Precision Using a Plasmonic Imaging Technique", Small, Jun. 2015 [available online Feb. 2015], vol. 11, No. 24, pp. 2878-2884 <DOI:10.1002/smll.201403016>.

Yetisen, A. et al., "Paper-Based Microfluidic Point-of-Care Diagnostic Devices", Lab on a Chip, Jun. 2013 [available online May 2013], vol. 13, No. 12, pp. 2210-2251 <DOI:10.1039/c3lc50169h>.

Zhang, Y. et al., "Membrane Lipid Homeostasis in Bacteria", Nature Reviews Microbiology, Mar. 2008, vol. 6, pp. 222-233 <DOI:10.1038/nrmicro 1839>.

Zordan, M. et al., "Detection of Pathogenic E. coli O157:H7 by a Hybrid Microfluidic SPR and Molecular Imaging Cytometry Device", Cytometry Part A, Jan. 2009 [available online Dec. 2008], vol. 75, pp. 155-162 <DOI:10.1002/cyto.a.20692>.

Zurek, L. et al., "Insects Represent a Link between Food Animal Farms and the Urban Environment for Antibiotic Resistance Traits", Applied and Environmental Microbiology, Jun. 2014, vol. 80, No. 12, pp. 3562-3567 <DOI:10.1128/AEM.00600-14>.

Syal, K., "Rapid Antimicrobial Susceptibility Testing Based on Bacterial Motion Tracking", Arizona State University, PhD Thesis, first published via ProQuest on Jul. 31, 2019 [retrieved Aug. 18, 2020], 142 pages, ProQuest publication No. 10285984.

U.S. Appl. No. 16/633,812, Notice of Allowance and Fees Due, Sep. 24, 2020.

U.S. Appl. No. 16/633,812, Notice Of References Cited, dated Jun. 18, 2020.

U.S. Appl. No. 16/633,812, Notice Of Allowance, dated Jun. 18, 2020.

Aghayee, S. et al., "Combination of Fluorescence Microscopy and Nanomotion Detection to Characterize Bacteria", Journal of Molecular Recognition, Oct. 2013, vol. 26, pp. 590-595 <DOI:10.1002/jmr.2306>.

Ah, U. et al., "Isothermal Micro Calorimetry—a New Method for MIC Determinations: Results for 12 Antibiotics and Reference Strains of E. coli and S. aureus", BMC Microbiology, May 2009, vol. 9, No. 106, 14 pages <DOI:10.1186/1471-2180-9-106>.

Álvarez-Barrientos, et al., "Applications of Flow Cytometry to Clinical Microbiology", Clinical Microbiology Reviews, Apr. 2000, vol. 13, No. 2, pp. 167-195 <DOI:10.1128/cmr.13.2.167-195.2000>.

Balouiri, M. et al., "Methods for in Vitro Evaluating Antimicrobial Activity: A Review", Journal of Pharmecutical Analysis, Apr. 2016 [available online Dec. 2015], vol. 6, pp. 71-79 <DOI:10.1016/j.jpha.2015.11.005>.

Barczak, K. et al., "RNA Signatures Allow Rapid Identification of Pathogens and Antibiotic Susceptibilities", Proceedings of the National Academy of Sciences of the United States of America, Apr. 2012, vol. 109, No. 16, pp. 6217-6222 <DOI:10.1073/pnas.1119540109>.

Barenfanger, J. et al., "Clinical and Financial Benefits of Rapid Bacterial Identification and Antimicrobial Susceptibility Testing", Journal of Clinical Microbiology, May 1999, vol. 37, No. 5, pp. 1415-1418 <DOI:10.1128/JCM.37.5.1415-1418>.

Bartlett, J. et al., "Seven Ways to Preserve the Miracle of Antibiotics", Clinical Infectious Diseases: an official publication of the Infectious Diseases Society of America, May 2013 [available online Feb. 2013], vol. 56, No. 10, pp. 1445-1450 <DOI:10.1093/cid/cit070>.

Bates, M. et al., "Rapid Infectious Diseases Diagnostics Using Smartphones", Annals of Translational Medicine, Sep. 2015, vol. 3, No. 15, pp. 3-7 <DOI:10.3978/j.issn.2305-5839.2015.07.07>.

Bauer, K. et al., "Review of Rapid Diagnostic Tests Used by Antimicrobial Stewardship Programs", Clinical Infectious Diseases, Oct. 2014, vol. 59, No. 3, pp. S134-S145 <DOI:10.1093/cid/ciu547>.

Berke, A. et al., "Hydrodynamic Attraction of Swimming Microorganisms by Surfaces", Physical Review Letters, Jul. 2008, vol. 101, No. 3, pp. 1-4 <DOI:10.1103/PhysRevLett.101.038102>.

Besant, J. et al., "Rapid Electrochemical Phenotypic Profiling of Antibiotic-Resistant Bacteria", Lab Chip, Jul. 2015 [available online May 2015], vol. 15, No. 13, pp. 2799-2807 <DOI:10.1039/C5LC00375J>.

Besser, R. et al., "*Escherichia coli* O157:H7 Gastroenteritis and the Hemolytic Uremic Syndrome: An Emerging Infectious Disease", Annual Review of Medicine, Feb. 1999, vol. 50, pp. 355-367 <DOI:10.1146/annurev.med.50.1.355>.

Boedicker, J. et al., "Detecting Bacteria and Determining Their Susceptibility to Antibiotics by Stochastic Confinement in Nanoliter Droplets Using Plug-Based Microfluidics", Lab on a Chip, Jul. 2008, vol. 8, No. 8, pp. 1265-1272 <DOI:10.1039/b804911d>.

(56) References Cited

OTHER PUBLICATIONS

Bonkat, G. et al., "Rapid Detection of Urinary Tract Pathogens Using Microcalorimetry: Principle, Technique and First Results", BJU International, Sep. 2012 [available online Feb. 2012], vol. 110, No. 6, pp. 892-897 <DOI:10.1111/j.1464-410X.2011.10902.x>.

Bradford, P. et al., "Colistin-Resistant Enterobacteriaceae: Correlation of β-Lactamase Production and Colistin Resistance among Isolates from a Global Surveillance Program", Antimicrobial Agents and Chemotherapy, Mar. 2016 [available online Feb. 2016], vol. 60, No. 3, pp. 1385-1392 <DOI:10.1128/AAC.01870-15>.

Buchan, B. et al., "Emerging Technologies for the Clinical Microbiology Laboratory", Clinical Microbiology Reviews, Oct. 2014, vol. 27, No. 4, pp. 783-822 <DOI:10.1128/CMR.00003-14>.

Bugrysheva, J. et al., "Rapid Antimicrobial Susceptibility Testing of Bacillus Anthracis, Yersinia Pestis, and Burkholderia Pseudomallei Using Laser Light Scattering Technology", Journal of Clinical Microbiology, Jun. 2016 [available online May 2016], vol. 54, No. 6, pp. 1462-1471 <DOI:10.1128/JCM.03251-15>.

Burg, T. et al., "Weighing of Biomolecules, Single Cells and Single Nanoparticles in Fluid", Nature, Apr. 2007, vol. 446, No. 7139, p. 1066 1069 <DOI:10.1038/nature05741>.

Carnes, E. et al., "Confinement-Induced Quorum Sensing of Individual *Staphylococcus aureus* Bacteria", Nature Chemical Biology, Jan. 2010 [available online Nov. 2009], vol. 6, pp. 41-45 <DOI:10.1038/nchembio.264>.

Casadevall, A. et al., "Passive Antibody Therapy for Infectious Diseases", Nature Reviews Microbiology, Sep. 2004, vol. 2, pp. 695-703 <DOI:10.1038/nrmicro974>.

CDC., "Antibiotic Resistance Threats in the United States, 2013", Centers for Disease Control and Prevention, 2013, 114 pages.

Chang, P. et al., "Imaging beyond the Proteome", Chemical Communications, Jul. 2012, vol. 48, No. 71, pp. 8864-8879 <DOI:10.1039/C2CC31845H>.

Chantell, C., "Multiplexed Automated Digital Microscopy for Rapid Identification and Antimicrobial Susceptibility Testing of Bacteria and Yeast Directly from Clinical Samples", Clinical Microbiology Newsletter, Oct. 2015, vol. 37, No. 20, pp. 161-167 <DOI:10.1016/j.clinmicnews.2015.10.001>.

Chen, C. et al., "Antimicrobial Susceptibility Testing Using High Surface-to-Volume Ratio Microchannels", Analytical Chemistry, Jan. 2010, vol. 82, No. 3, pp. 101-1019 <DOI:10.1021/ac9022764>.

Chiang, Y.-L. et al., "Innovative Antimicrobial Susceptibility Testing Method Using Surface Plasmon Resonance", Biosensors & Bioelectronics, Mar. 2009 [available online Oct. 2008], vol. 24, No. 7 pp. 1905-1910 <DOI:10.1016/j.bios.2008.09.020>.

Choi, J. et al., "A Rapid Antimicrobial Susceptibility Test Based on Single-Cell Morphological Analysis", Science Translational Medicine, Dec. 2014, vol. 6, No. 267, pp. 1-13 <DOI:10.1126/scitranslmed.3009650>.

Choi, J. et al., "Rapid Antibiotic Susceptibility Testing by Tracking Single Cell Growth in a Microfluidic Agarose Channel System", Lab on a Chip, Jan. 2013 [available online Nov. 2012], vol. 13, No. 2, pp. 280-287 <DOI:10.1039/c2lc41055a>.

Chotinantakul, K. et al., "Advanced Amperometric Respiration Assay for Antimicrobial Susceptibility Testing", Analytical Chemistry, Sep. 2014, vol. 86, No. 20, pp. 10315-10322 <DOI:10.1021/ac502554s>.

Clarridge, J., "Impact of 16S rRNA Gene Sequence Analysis for Identification of Bacteria on Clinical Microbiology and Infectious Diseases", Clinical Microbiology Reviews, Oct. 2004, vol. 17, No. 4, pp. 840-862 <DOI:10.1128/CMR.17.4.840-862.2004>.

Cybulski, J. et al., "Foldscope : Origami-Based Paper Microscope", PLoS One, Jun. 2014, vol. 9, No. 6, pp. e98781 <DOI:10.1371/journal.pone.0098781>.

Cywes-Bentley, C. et al., "Antibody to a Conserved Antigenic Target Is Protective against Diverse Prokaryotic and Eukaryotic Pathogens", Proceedings of the National Academy of Sciences of the United States of America, May 2013, vol. 110, pp. E2209-18 <DOI:10.1073/pnas.1303573110>.

Dalgaard, P. et al., "Estimation of Bacterial Growth Rates from Turbidimetric and Viable Count Data", International Journal of Food Microbiology, Nov. 1994, vol. 23, pp. 391-404 <DOI:10.1016/0168-1605(94)90165-1>.

Dambrosio, M. et al., "Point-of-Care Quantification of Blood-Borne Filarial Parasites with a Mobile Phone Microscope", Science Translational Medicine, May 2015, vol. 7, No. 286, pp. 286re4 <DOI:10.1126/scitranslmed.aaa3480>.

Daniels, R., "Surviving the First Hours in Sepsis: Getting the Basics Right (an Intensivist's Perspective)", Journal of Antimicrobial Chemotherapy, Apr. 2011, vol. 66, No. 2, pp. 11-23 <DOI:10.1093/jac/dkq515>.

Daugelavicius, R. et al., "Stages of Polymyxin B Interaction with the *Escherichia coli* Cell Envelope", Antimicrobial Agents and Chemotherapy, Nov. 2000, vol. 44, No. 11, pp. 2969-2978 <DOI:10.1128/aac.44.11.2969-2978.2000>.

Delcour, A., "Outer Membrane Permeability and Antibiotic Resistance", Biochimica et Biophysica Acta, May 2009 [available online Nov. 2008], vol. 1794, No. 5, pp. 808-816 <DOI:10.1016/j.bbapap.2008.11.005>.

Douglas, I. et al., "Rapid Automated Microscopy for Microbiological Surveillance of Ventilator-Associated Pneumonia", American Journal of Respiratory and Critical Care Medicine, Mar. 2015, vol. 191, No. 5, pp. 566-573 <DOI:10.1164/rccm.201408-1468OC>.

Eigner, U. et al., "Analysis of the Comparative Workflow and Performance Characteristics of the VITEK 2 and Phoenix Systems Analysis of the Comparative Workflow and Performance Characteristics of the VITEK 2 and Phoenix Systems", Journal of Clinical Microbiology, Aug. 2005, vol. 43, No. 8, pp. 3829-3834 <DOI:10.1128/JCM.43.8.3829-3834.2005>.

Ertl, P. et al., "Rapid Antibiotic Susceptibility Testing via Electrochemical Measurement of Ferricyanide Reduction by *Escherichia coli* and Clostridium Sporogenes", Analytical Chemistry, Oct. 2000 [available online Sep. 2000], vol. 72, No. 20, pp. 4957-4964 <DOI:10.1021/ac0003596>.

Etayash, H. et al., "Microfluidic Cantilever Detects Bacteria and Measures Their Susceptibility to Antibiotics in Small Confined Volumes", Nature Communications, Oct. 2016, vol. 7, Article No. 12947 <DOI:10.1038/ncomms12947>.

Fantner, G. et al., "Kinetics of Antimicrobial Peptide Activity Measured on Individual Bacterial Cells Using High-Speed Atomic Force Microscopy", Nature Nanotechnology, Mar. 2010, vol. 5, pp. 280-285 <DOI: 10.1038/NNANO.2010.29>.

Fleming, A., "On the Antibacterial Action of Cultures of a Penicillium, with Special Reference to Their Use in the solation of B. Influenzae", The British Journal of Experimental Pathology, Jun. 1929, vol. 10, No. 3, pp. 226-336.

Flores-Mireles, A. et al., "Urinary Tract Infections: Epidemiology, Mechanisms of Infection and Treatment Options", Nature Reviews Microbiology, May 2015, [available online Apr. 2015], vol. 13, pp. 269-284 <DOI:10.1038/nrmicro3432>.

Fluit, A. C. et al., "Molecular Detection of Antimicrobial Resistance", Clinical Microbiology Reviews, Oct. 2001, vol. 14, pp. 836-871 <DOI:10.1128/CMR.14.4.836-871.2001>.

Fredborg, M. et al., "Rapid Antimicrobial Susceptibility Testing of Clinical Isolates by Digital Time-Lapse Microscopy", European Journal of Clinical Microbiology & Infectious Diseases, Dec. 2015 [available online Sep. 2015], vol. 34, pp. 2385-2394 <DOI:10.1007/s10096-015-2492-9>.

Fredborg, M. et al., "Real-Time Optical Antimicrobial Susceptibility Testing", Journal of Clinical Microbiology, Jul. 2013 [available online Jun. 2013], vol. 51, No. 7, pp. 2047-2053 <DOI:10.1128/JCM.00440-13>.

Fredricks, B. et al., "Rapid Pyrazinamide Susceptibility Testing of Mycobacterium Tuberculosis by Flow Cytometry", Journal of Microbiology Methods, Nov. 2006 [available online May 2006], vol. 67, No. 2, pp. 266-272 <DOI:10.1016/j.mimet.2006.03.020>.

Fruh, V. et al., "How to Catch a Membrane Protein in Action: A Review of Functional Membrane Protein Immobilization Strategies and Their Applications", Chemical Reviews, Feb. 2011 [available online Sep. 2010], vol. 111, pp. 640-656 <DOI:10.1021/cr900088s>.

(56) References Cited

OTHER PUBLICATIONS

Frymier, P. et al., "Three-Dimensional Tracking of Motile Bacteria near a Solid Planar Surface", Proceedings of the National Academy of Sciences of the United States of America, 1995, vol. 92, pp. 6195-6199 <DOI:10.1073/pnas.92.13.6195>.

Godin, M. et al., "Using Buoyant Mass to Measure the Growth of Single Cells", Nature Methods, May 2010 [available online Apr. 2011], vol. 7, No. 5, pp. 387-390 <DOI:10.1038/nmeth.1452>.

* cited by examiner

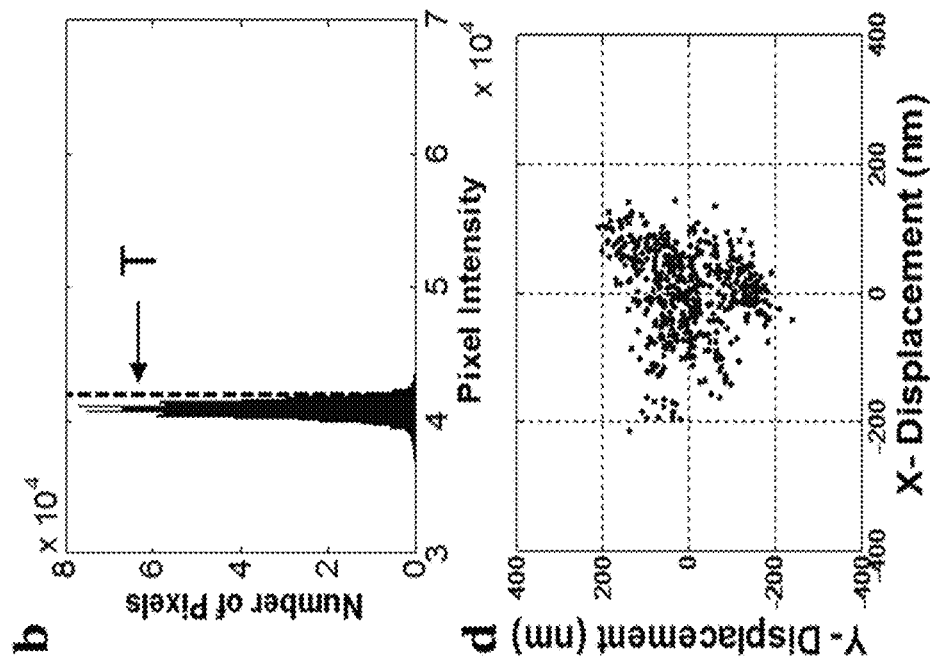
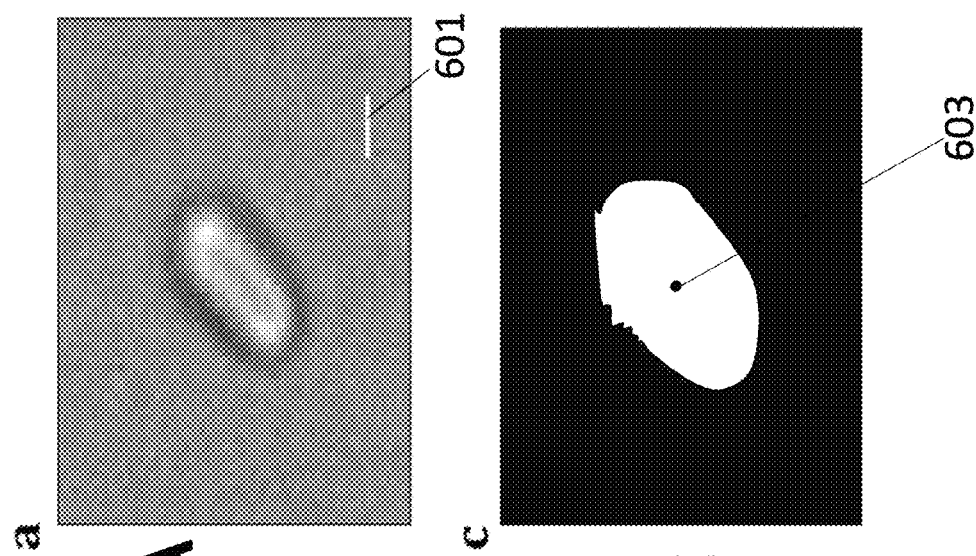
FIG. 6A   FIG. 6B   FIG. 6C   FIG. 6D

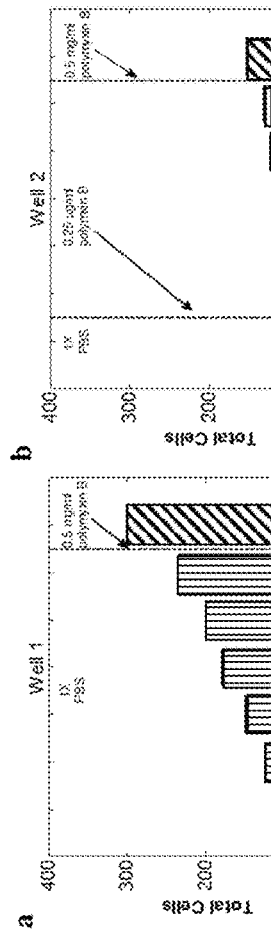
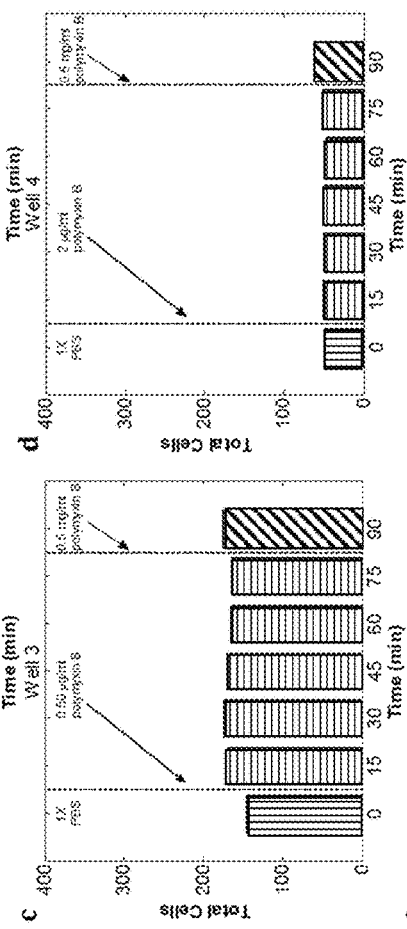
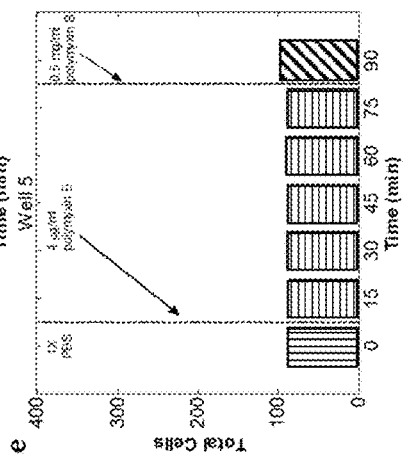
FIG. 8A  FIG. 8B  FIG. 8C  FIG. 8D  FIG. 8E

FIG. 9A
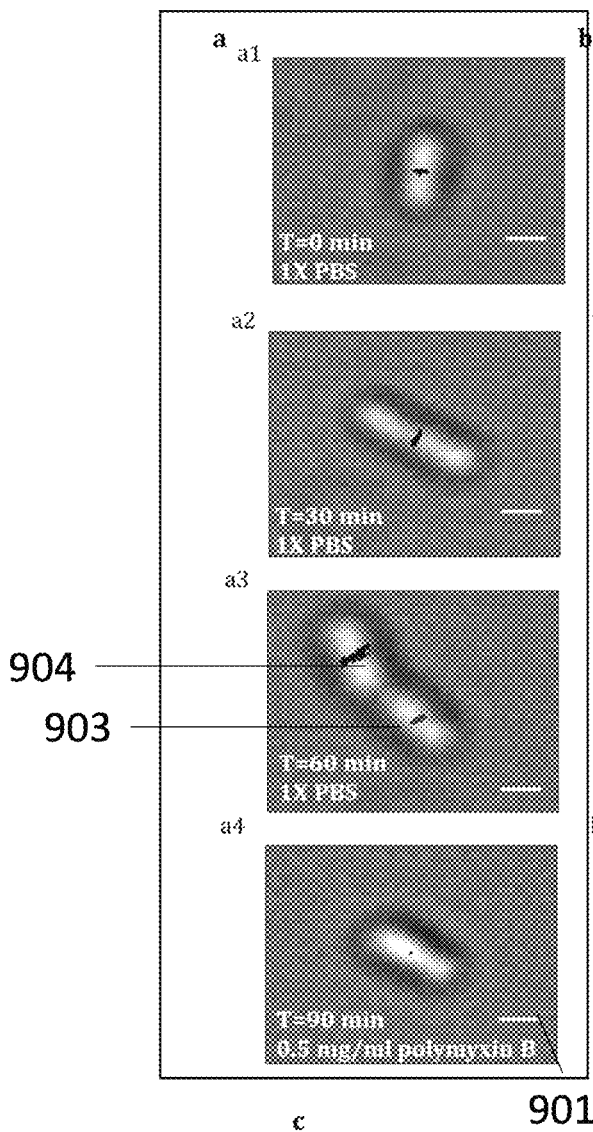
FIG. 9B
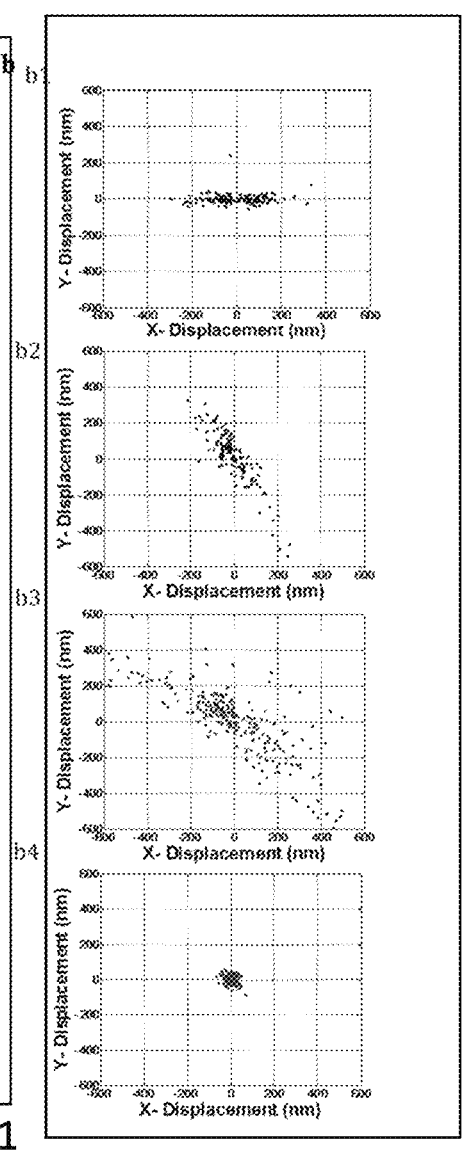
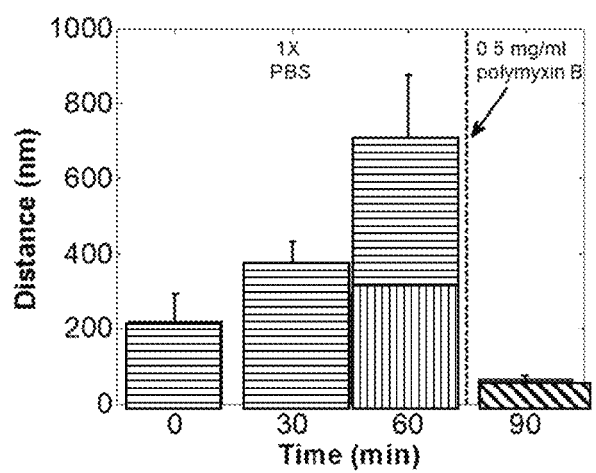
FIG. 9C

FIG. 10A 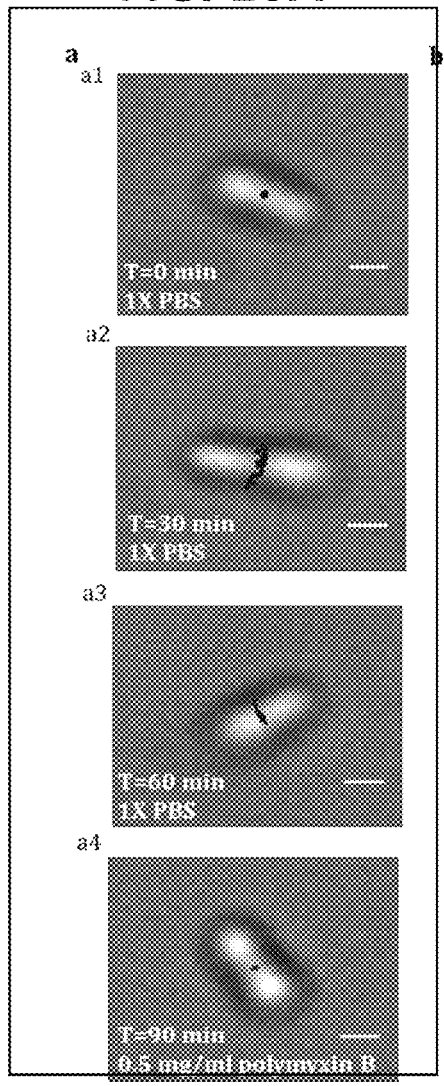 FIG. 10B 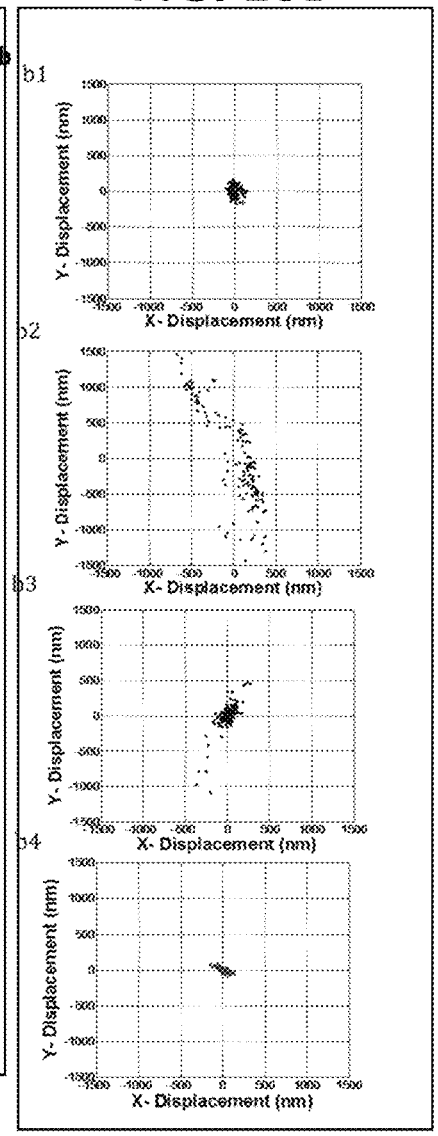
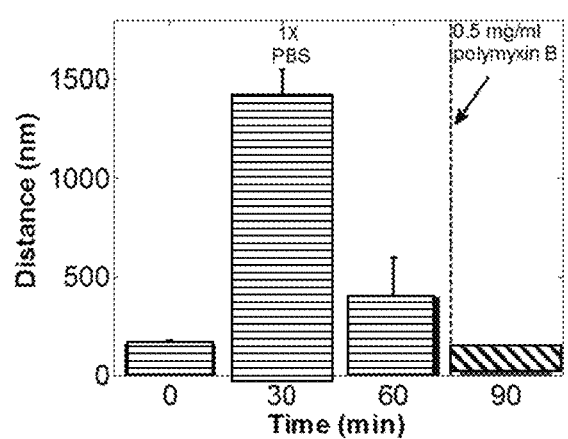
FIG. 10C

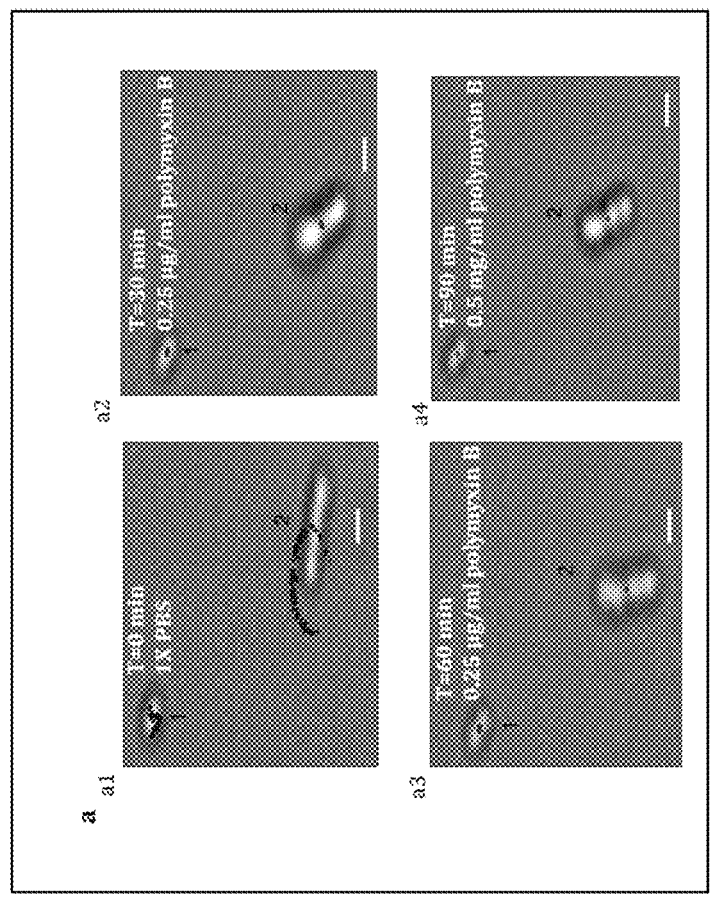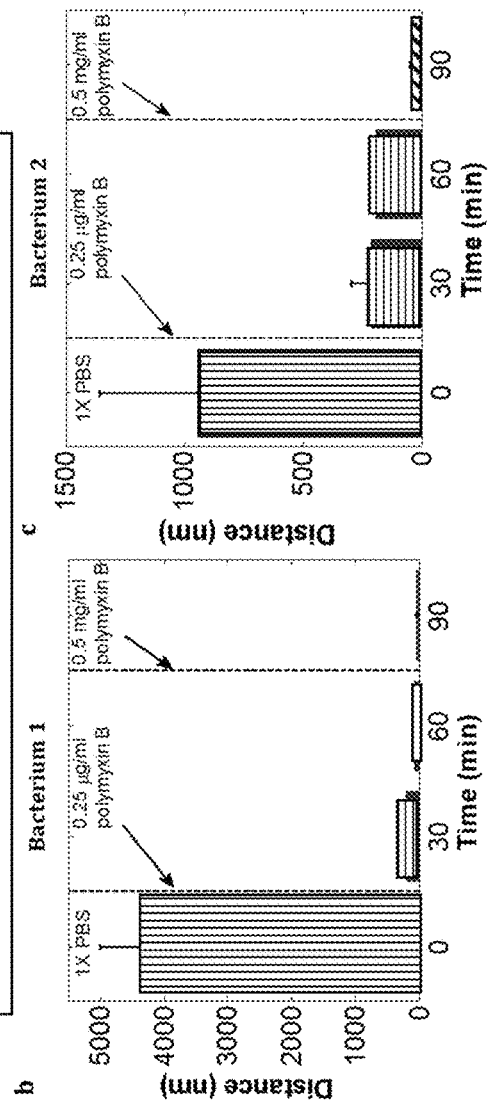
FIG. 11A
FIG. 11B
FIG. 11C

| polymyxin B concentration (μg/ml) | Replicate Number | | |
|---|---|---|---|
| | 1 | 2 | 3 |
| 0 | Colony Growth | Colony Growth | Colony Growth |
| 0.125 | Colony Growth | Colony Growth | Colony Growth |
| 0.25 | Colony Growth | Colony Growth | Colony Growth |
| 0.50 | No Colony Growth | Colony Growth | Colony Growth |
| 1 | Colony Growth | No Colony Growth | No Colony Growth |
| 2 | No Colony Growth | No Colony Growth | No Colony Growth |
| 4 | No Colony Growth | No Colony Growth | No Colony Growth |
| 8 | No Colony Growth | No Colony Growth | No Colony Growth |
| 16 | No Colony Growth | No Colony Growth | No Colony Growth |
| 32 | No Colony Growth | No Colony Growth | No Colony Growth |

FIG. 16

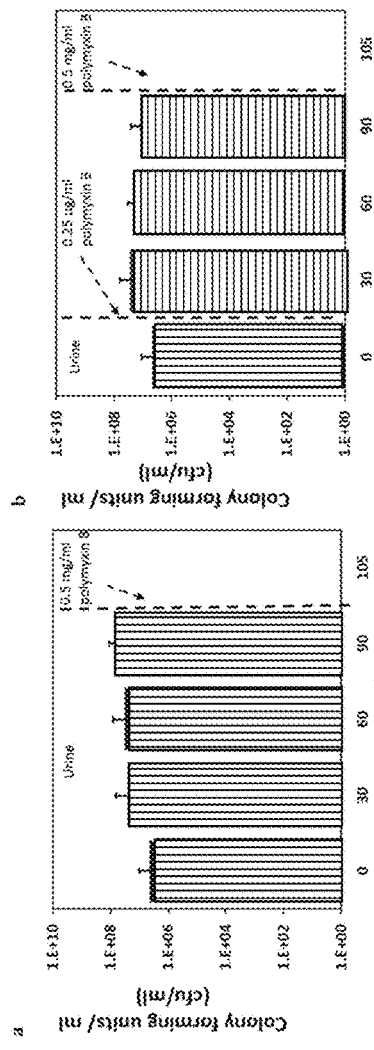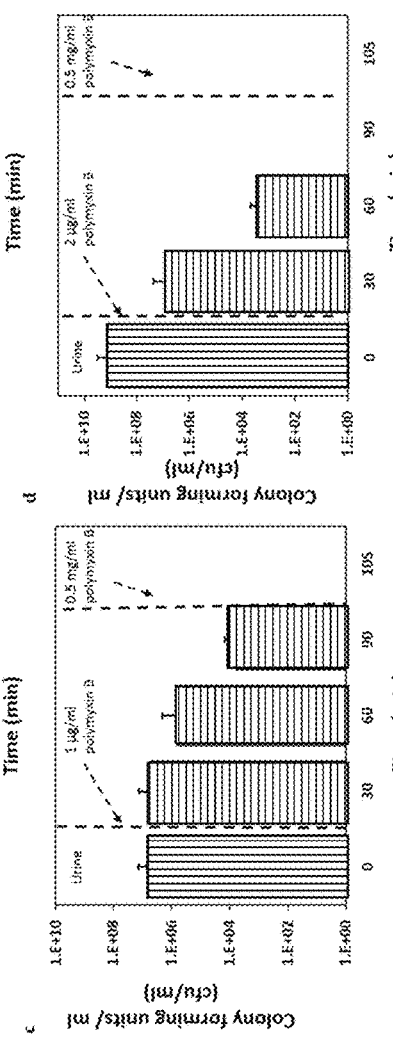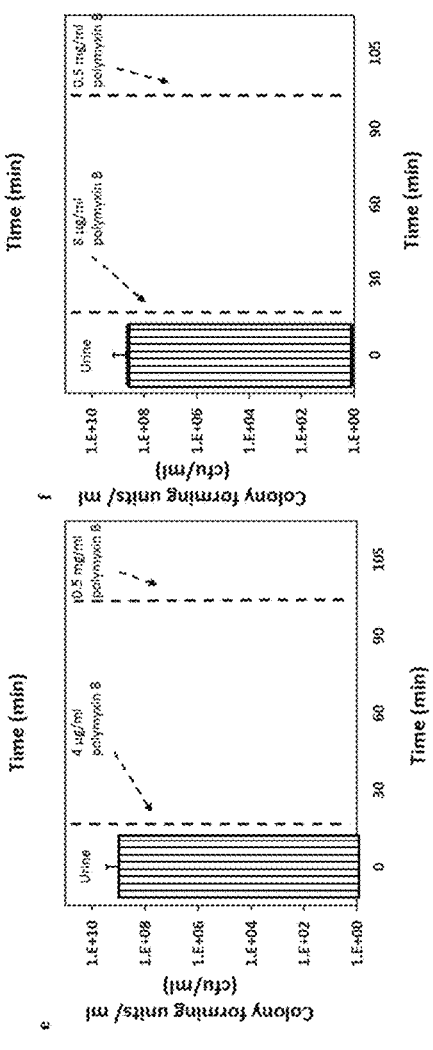
FIG. 17A  FIG. 17B  FIG. 17C  FIG. 17D  FIG. 17E  FIG. 17F

RAPID ANTIBIOTIC SUSCEPTIBILITY TESTING BY TRACKING SUB-MICRON SCALE MOTION OF SINGLE BACTERIAL CELLS

STATEMENT OF RELATED APPLICATIONS

This application is a continuation of Ser. No. 16/633,812, filed Jan. 24, 2020, now U.S. Pat. No. 10,947,576, which is a 371 of PCT/US18/43638, filed Jul. 25, 2018, which claims benefit of U.S. Provisional Patent Application No. 62/536,895, filed Jul. 25, 2017, the disclosures of which are hereby incorporated herein by reference in their entireties.

TECHNICAL FIELD

The present invention relates to antibiotic susceptibility testing (AST), and, more particularly, to a method and apparatus for rapid antibiotic susceptibility testing by tracking sub-micron scale motion of single bacterial cells.

BACKGROUND

Bacterial infections are a global disease burden, causing 3 million patient deaths and 30 million patient hospitalizations annually.[1] Effective treatment of bacterial infections requires prescription of appropriate antibiotics at the disease onset.[2] This requirement is especially critical for patients with sepsis or experiencing septic shock, where mortality increases 7.6% for every hour of delayed antibiotic treatment.[3-5] Antibiotic susceptibility testing (AST) is used to identify antibiotic resistant bacterial strains and to enable treatment with appropriate antibiotics.[2,8] However, current AST technologies take 1-3 days due to their dependence on bacterial culturing.[7,8] Without rapid AST, physicians often prescribe broad-spectrum antibiotics,[9,10] which has contributed to the acceleration of bacterial antibiotic resistance.[4,9] A faster AST technique will empower physicians to prescribe, preferably within 1-2 hours or less, effective narrow-spectrum antibiotics.[11,12]

Emerging AST technologies based on detecting bacterial growth rate via measuring cell numbers[13-15], cell size[18,17], and molecular or biochemical markers (RNA,[18,19] DNA,[20] or redox molecules[21-24]) are being developed. Several culture-free, metabolism-based AST technologies, which use bacterial nano-motion,[25-27] heat-signatures,[28,29] and biochemical profiles,[30] have also been pursued. While these technologies offer potential solutions, a rapid (e.g., 2 hours) and robust AST technology requires further development.[8]

Hydrodynamic[31,32] and motility-induced long-range motions[31,33] of alive bacterial cells in the range of several microns near a surface have been studied using particle image velocimetry algorithms[34] and digital holographic imaging technologies.[32] However, short-range motion (a few nm) of surface-attached bacterial cells and their correlation to bacterial metabolism have only been recently studied using highly sensitive tools, such as atomic force microscopy[26,36] and plasmonic imaging and tracking (PIT).[26,36]

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

A method for rapid antibiotic susceptibility testing by tracking sub-micron scale motion of single bacterial cells including obtaining a biological sample from a subject including live bacteria is disclosed. Different doses of antibiotic are added to a multi-well glass slide and adding portions of the biological sample to the wells. Bacterial cells are tethered onto the glass surface. The tethered bacterial cells are imaged and tracked. Bacterial sub-micron motion of tethered cells is measured at the different doses. A processor performs statistical analysis on a population of cells for each antibiotic dose to generate an antibiotic dose curve proportional to the motion changes, where the antibiotic dose curve plots data including a decrease in movement over time indicating a proportional effectiveness of an antibiotic applied to a well.

Motility-induced motion of bacterial cells in solution has been previously studied using various techniques.[32,48] Bacterial cells have also been studied by attaching them firmly to a surface to enable clear optical imaging of the cells.[45] However, none of these approaches have quantified the sub-μm motion of surface-tethered bacterial cells and applied it for AST. A key enabling step in the present work is the optimization of the antibody and APTES surface chemistry to achieve loosely tethered bacterial cells for continuous imaging and tracking of the sub-micron motion of each cell.

Demonstrated herein is a method for rapid (within 2 h) AST of clinically-relevant bacteria, $E.\ coli$ O157:H7[37] and UPEC, by quantifying the sub-μm motion of single cells. Compared to AFM, which measures cantilever deflections due to bacterial nano-motion in z direction, the method disclosed herein can simultaneously image multiple bacterial cells. Compared to a previously described PIT system,[26] the present method is simpler in both instrumentation and sensor chip preparation. The present work has focused on $E.\ coli$ O157:H7[37] and UPEC with the polymyxin B antibiotic. Future work will include other bacteria, including $Staphylococcus\ aureus$,[25-27] to demonstrate the broad application of the present method.

The sub-μm motion of surface-tethered bacterial cells is measured using a simple bright-field imaging setup together with automated image processing algorithms and determine the correlation of the sub-μm motion with bacterial viability and metabolism. The method is applied to clinically relevant bacteria, $Escherichia\ coli$ O157:H7[37] and uropathogenic $E.\ coli$ (UPEC), and the antibiotic, polymyxin B.[38] UPEC accounts for ~75% of all urinary tract infections (UTIs) and affects over 10 million people worldwide.[38] Polymyxin B is a cationic polypeptide antibiotic closely related to colistin (polymyxin E), which is an important last-line antibiotic.[39] Colistin resistance has recently been reported in bacterial strains that cause UTIs in patients.[40,41,42]

To demonstrate rapid AST, a coupling chemistry was developed to tether bacterial cells loosely onto the glass surface and imaging processing algorithms to quantify the sub-μm motion of tethered cells. The antibiotic-induced sub-micron motion changes of individual cells were further measured, antibiotic dose dependency of the motion changes was studied, clinically relevant minimum bactericidal concentration of the antibiotic was determined, and rapid AST performed on human urine samples spiked with UPEC cells.

BRIEF DESCRIPTION OF THE DRAWINGS

While the novel features of certain embodiments of the invention are set forth with particularity in the appended claims, the invention, both as to organization and content, will be better understood and appreciated, along with other objects and features thereof, from the following detailed description taken in conjunction with the drawings, in which:

FIG. 2A' shows a more detailed plot of the displacement of the cell center of FIG. 2A over 20 secs, reflecting the sub-μm motion of the cell.

FIG. 6A-FIG. 6D show an example image processing of bacterial cells to quantitate X and Y displacement and movement.

FIG. 8A-FIG. 8E show examples of dose dependency of a total number of UPEC cells in the images.

FIG. 9A-FIG. 9C illustrate changes in sub-μm motion of a replicating UPEC cell partially tethered on the surface.

FIG. 10A-FIG. 10C illustrate changes in sub-μm motion of a replicating UPEC cell partially tethered on the surface.

FIG. 11A-FIG. 11C illustrate a decrease in sub-μm motion of surface-tethered UPEC cells exposed to 0.25 μg/ml polymyxin B.

FIG. 16 shows a table illustrating growth inhibition and bactericidal activity of the antibiotic polymyxin B.

FIG. 17A-FIG. 17F are plots of bactericidal activity of polymyxin B against UPEC in spiked urine samples.

FIG. 20A-FIG. 20C show motion changes of loosely and completely tethered bacterial cells.

Figure 1:
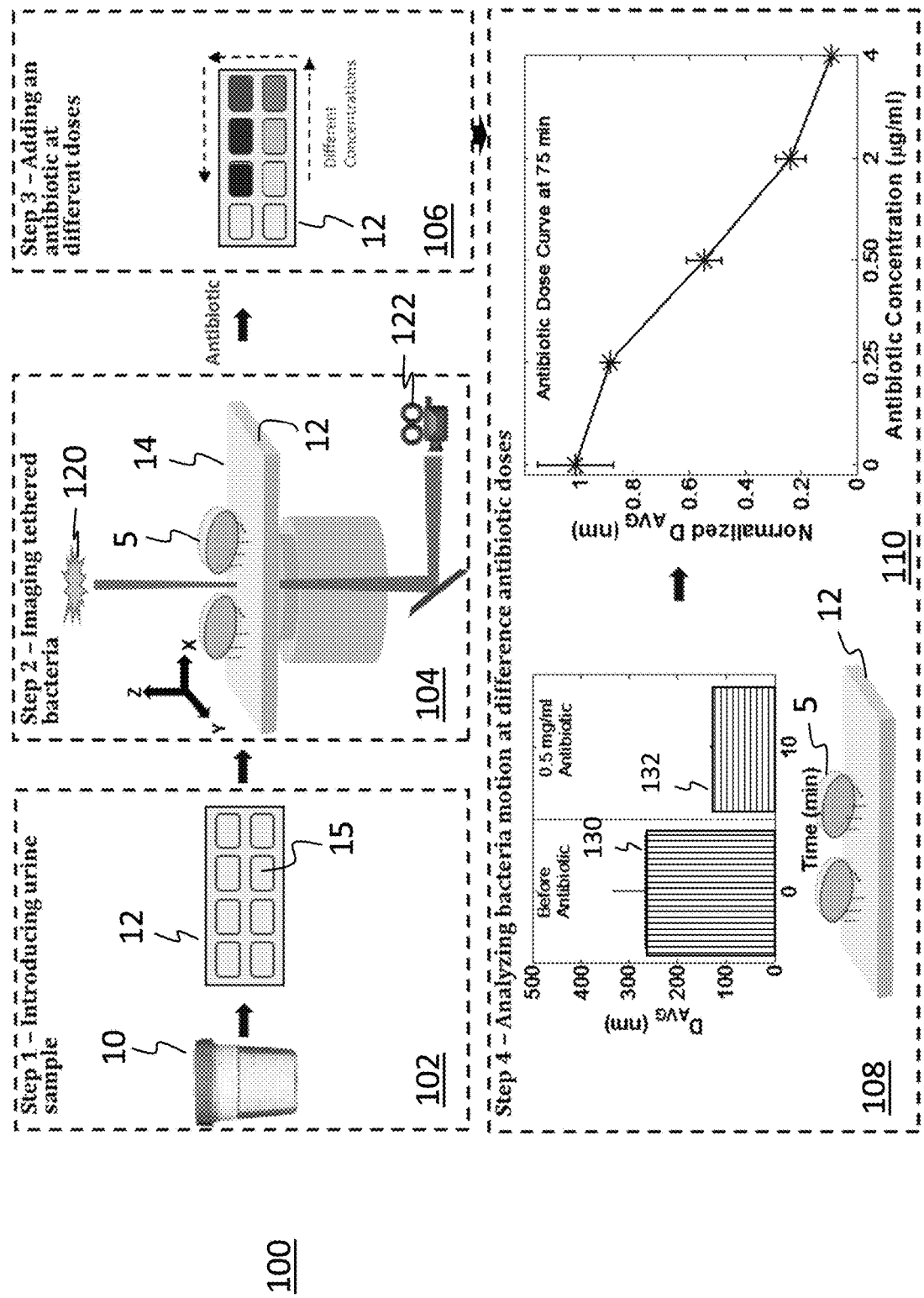
FIG. 1 schematically shows an example of an experimental setup to image and track bacterial cell sub-μm motions.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

The following disclosure describes a device for antibiotic susceptibility testing (AST). Several features of methods and systems in accordance with example embodiments are set forth and described in the figures. It will be appreciated that methods and systems in accordance with other example embodiments can include additional procedures or features different than those shown in the figures. Example embodiments are described herein with respect to a rapid AST apparatus and method for measuring the sub-micron motion of surface-tethered bacterial cells. However, it will be understood that these examples are for the purpose of illustrating the principles, and that the invention is not so limited.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of microarray technology:

The articles "a" or "an" and the phrase "at least one" as used herein refers to one or more.

As used herein, (3-Aminopropyl)triethoxysilane (APTES) is an aminosilane frequently used in the process of silanization, the functionalization of surfaces with alkoxysilane molecules.

As used herein, "AST" means antibiotic susceptibility testing of cells.

"Deep Learning," as used herein, is used in its generally accepted meaning as a class of machine learning algorithms using a cascade of many layers of nonlinear processing units, as for example neural networks and adaptive processors, that can be based on unsupervised or supervised learning, pattern analysis applications and the like.

"Minimal Inhibitory Concentration (MIC)" is used in its generally accepted meaning as the lowest drug concentration that prevents visible microorganism growth.

"Minimum Bactericidal Concentration (MBC)" is used in its generally accepted meaning as the lowest concentration of an antibacterial agent required to kill a particular bacterium.

As used herein, "plurality" is understood to mean more than one. For example, a plurality refers to at least two, three, four, five, ten, 25, 50, 75, 100, 1,000, 10,000 or more.

As used in this specification, the terms "processor" and "computer processor" encompass a personal computer, a tablet computer, a smart phone, a microcontroller, a microprocessor, a field programmable object array (FPOA), a digital signal processor (DSP), an application-specific integrated circuit (ASIC), a field programmable gate array (FPGA), a programmable logic array (PLA), or any other digital processing engine, device or equivalent capable of executing software code including related memory devices, transmission devices, pointing devices, input/output devices, displays and equivalents.

"Obtaining" is understood herein as manufacturing, purchasing, or otherwise coming into possession of.

Example Embodiments

Referring now to FIG. 1, an example of performed an experimental setup to image and track bacterial cell sub-µm motions is schematically shown. There shown is a multistep method of 100 including the act of introducing a biological sample 102, such as a urine sample, imaging tethered bacteria 104, introducing an antibiotic 106, analyzing bacterial motion at difference antibiotic doses 108 and plotting an antibiotic dose curve 110. At step 1, human urine samples 10, for example, are spiked with live bacteria and added to a multi-well glass slide 12, thus allowing bacterial cells 5 to tether onto the glass surface 14. At step 2, wells 15 of the slide are imaged by light microscopy 120, and the motions of the tethered bacterial cells are quantitated via image analysis as indicated by a camera 122. The camera may include or be connected to a processor for image processing and other software operations. At step 3, different doses of antibiotics are added to the wells on the slides, and the changes in bacterial cell motions are recorded. At step 4, image analysis reveals that the bacterial cell population decreases motion (represented by average distance—$D_{AVG}$; discussed below) upon antibiotic exposure. Bars 130 show motion before adding antibiotic. Bars 132 show motion after antibiotic. Statistical analysis on a population of cells for each antibiotic dose is performed, and an antibiotic dose curve is obtained. Plot 110 represents a plot of normalized $D_{AVG}$ in nm plotted against antibiotic concentration in µg/ml. Note that after 75 minutes the normalized $D_{AVG}$ decreases substantially from a normalized value of 1 to below 0.2 nm, as the antibiotic concentration increases from 0 to 4 µg/ml.

Figure 2A:
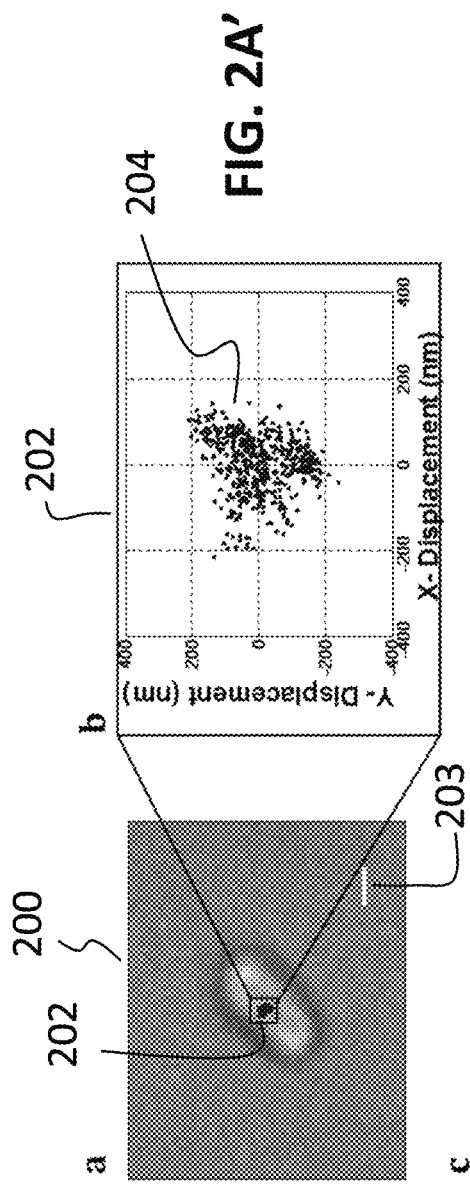
FIG. 2A shows an image of an *E. coli* O157:H7 bacterial cell with superimposed motion of the cell center over 20 sec shown as darkened dots.

Referring now to FIG. 2A an image of an *E. coli* O157:H7 bacterial cell with superimposed motion of the cell center over 20 sec shown as darkened dots is shown. *E. coli* O157:H7 cells 202 tethered to the glass slide were imaged. The cell 200, exhibits motion as represented by dots in frame 202. Scale Bar 203 is 1 µm. 43 The center of each bacterial cell was identified in each image frame (described in more detail below with reference to FIG. 6A-FIG. 6D) and plotted as data points 204 in FIG. 2A'.

FIG. 2A' shows a more detailed plot of the displacement of the cell center of FIG. 2A over 20 secs, reflecting the sub-µm motion of the cell. As there shown, plot 202 plots motion data 204 in nm in X and Y coordinates ranging from −400 nm to 400 nm. The center positions of the bacterial cell (center) at different moments are shown and reveal the sub-µm scale motion of the cell. For quantitative analysis of the sub-µm motion of the bacterial cell, "Distance" is defined as the root-mean-square of the position over 20 seconds. Note that the motion ranges from about −200 nm to 200 nm displacement along both coordinates.

Figure 2B:
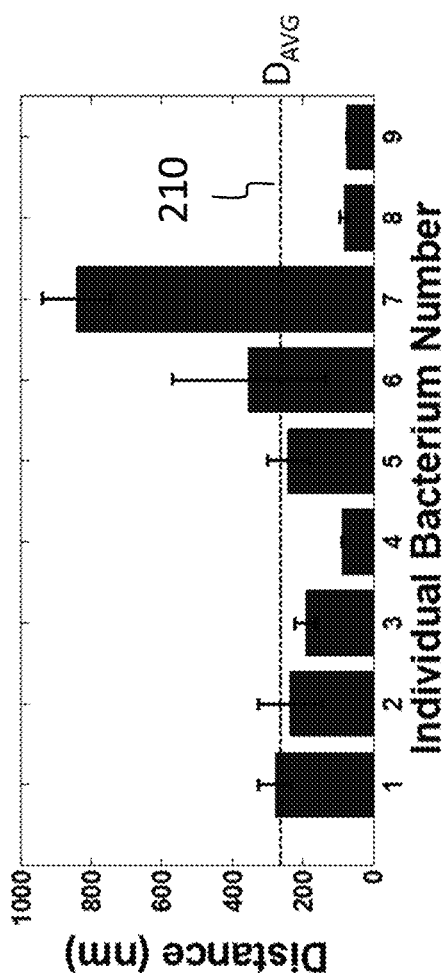
FIG. 2B shows a plot of distance, defined as the root-mean-square of the displacement of cell center over 20 secs, of nine different bacterial cells. The dashed line represents average distance ($D_{AVG}$) of the nine bacterial cells.

FIG. 2B shows a plot of distance, defined as the root-mean-square of the displacement of cell center over 20 secs, of nine different bacterial cells. The dashed line 210 represents average distance ($D_{AVG}$) of the nine bacterial cells. The distances for different bacterial cells varied from 75 to 842 nm, with an average distance ($D_{AVG}$) of 265 nm. For quantitative analysis of the sub-µm motion of the bacterial cell, we defined "Distance" as the root-mean-square of the position over 20 seconds. For an individual bacterial cell, the distance varied with time over triplicate 20 s recordings and reached its peak within 5 seconds By tracking the position of a marker (pillars attached inside a microfluidic cassette) in the image, the measured distance error was −25 nm (described below with reference to FIG. 7A-FIG. 7B). That is much smaller than the average distance (278 nm) of a typical bacterial cell shown in FIG. 2A. These results demonstrated that the bacteria cells tethered on the surface experienced sub-µm motion, and the imaging algorithm accurately tracked the motion.

Figures 3A, 3B:
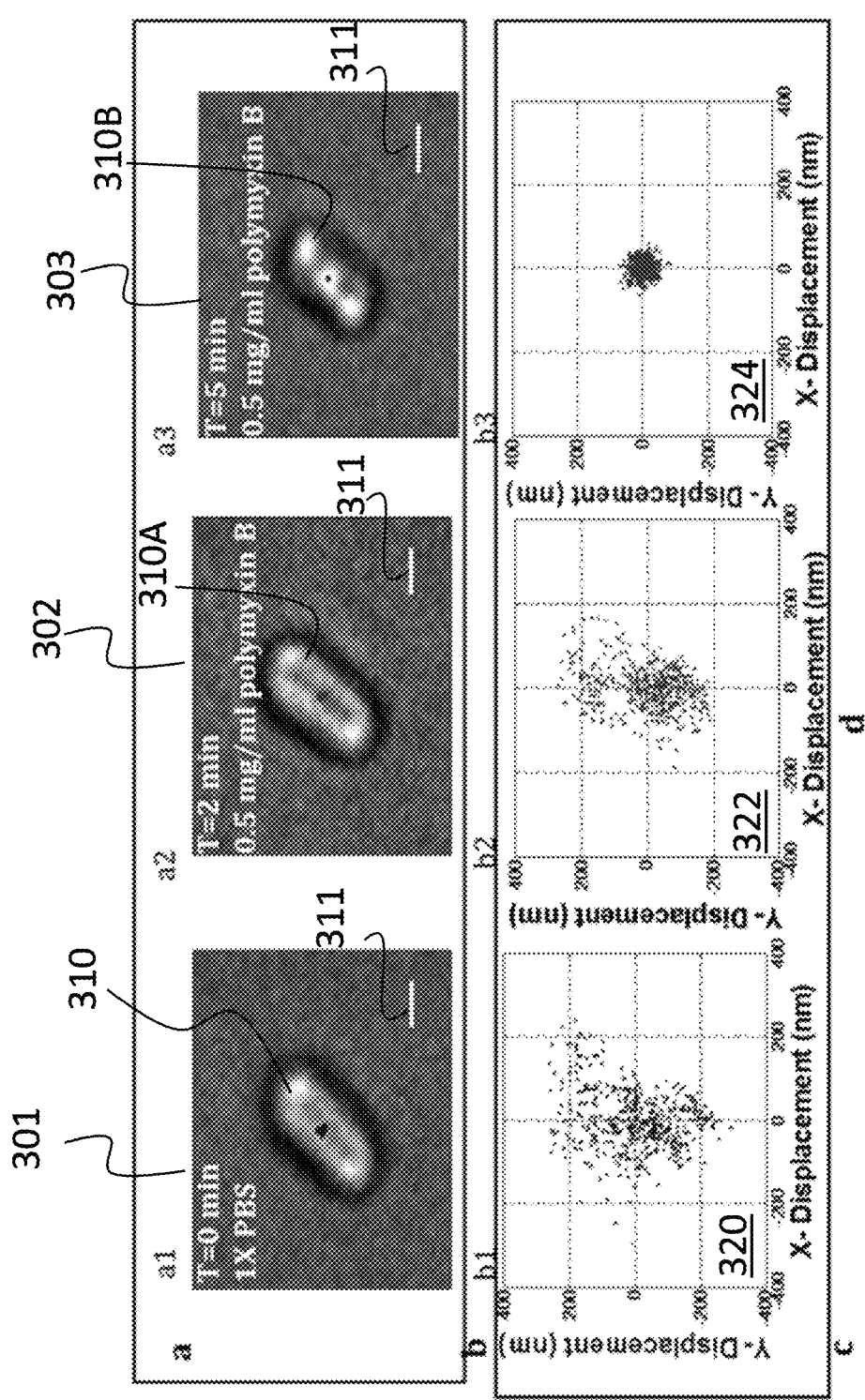
FIG. 3A shows images of a bacterial cell and displacement of the cell center in 1×PBS before (0 min) and after polymyxin B addition (2 and 5 min).
FIG. 3B shows displacement plots of the cell center recorded over 20 sec.

Referring now to FIG. 3A, images of a bacterial cell and displacement of the cell center in 1×PBS before (0 min) and after polymyxin B addition (2 and 5 min) are shown. Images 301, 302, 303 of a bacterial cell and displacement of the cell center 310 in 1×PBS before (0 min) and after polymyxin B addition (2 and 5 min). Antibiotic effects on the sub-µm motion were examined using a lethal dose of polymyxin B (0.5 mg/ml). Images 301, 302, 303 show the bright-field images of an alive bacterial cell before, 2 min, and 5 min, respectively after exposure to 0.5 mg/ml polymyxin B, where the positions of the bacterial cell before and after the exposure to polymyxin B, represented by indicia 310, 310A and 310B respectively. Scale bar 311 is set at 1 µm. #, p=0.065.

FIG. 3B shows displacement plots of the cell center recorded over 20 sec. The corresponding sub-µm motion and positions of the bacterial cell are more clearly shown in plots 320,322,324.

Figure 3D:
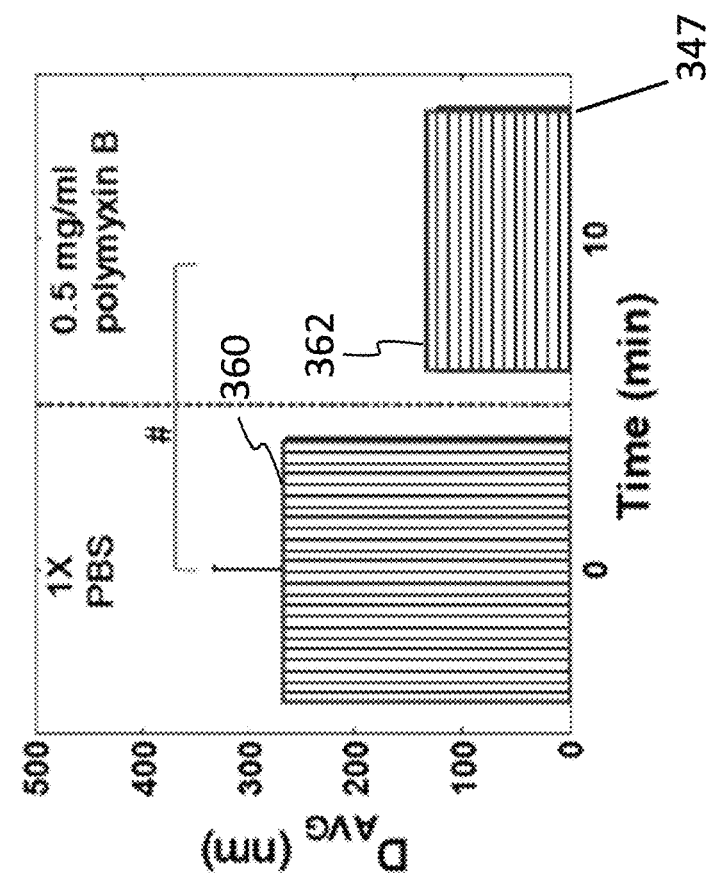
FIG. 3D shows average distance ($D_{AVG}$) of nine cells before and 10 min after the addition of polymyxin B (0.5 mg/ml).
Figure 3C:
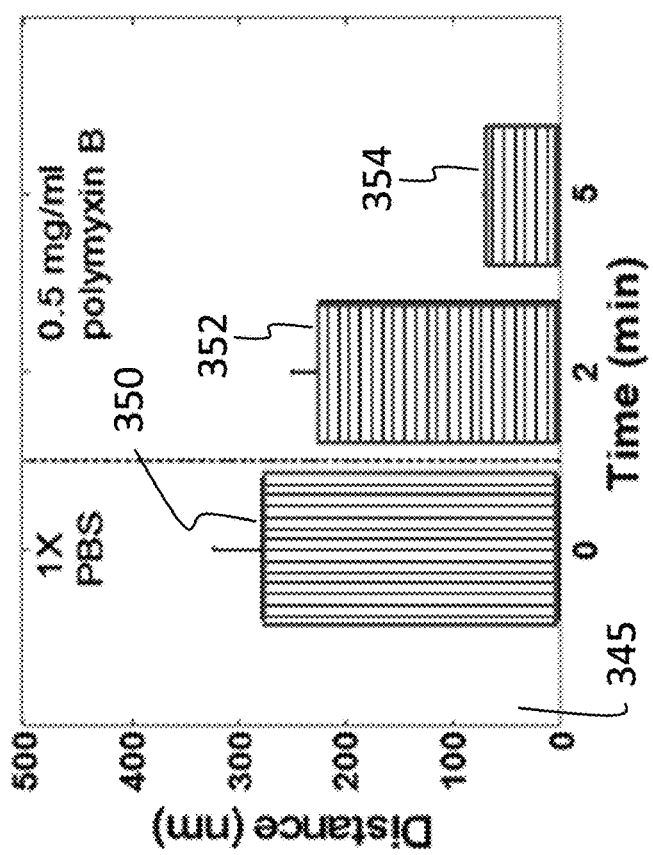
FIG. 3C shows distances of the cell motion at 0, 2, and 5 min.

FIG. 3C shows distances of the cell motion at 0, 2, and 5 min. The average *E. coli* O157:H7 distance over 20 sec. in 1×PBS was 278 nm as indicated by bar 350, which reduced to 225 nm within 2 min after addition of 0.5 mg/ml polymyxin B, indicated by bar 352 and further to 65 nm at 5 min post-antibiotic exposure as plotted in plot 324 and represented by bar 354. The remaining motion (65 nm) indicated that the bacteria had ceased activity since this amount of motion was likely due to the Brownian motion as a fixed object in the image had a motion of 25 nm (described below with reference to FIG. 7A-FIG. 7B). To ensure complete killing of the bacteria after 5 min exposure to the high, lethal dose of polymyxin B, overnight culturing of the cells yielded no viable cells. These results indicated that the sub-μm motion in the range of 50-65 nm is a good signature of a bacterial metabolic state.

Extrapolating further information from the results of FIG. 3C, in operation, a processor can be operated to perform statistical analysis on a population of cells for each antibiotic dose to generate an antibiotic dose curve proportional to the motion changes as described above. Further, using an imaging device and a processor, a distance range of bacterial cell motion can be determined as shown in the range of about 50 nm to about 65 nm (likely due to the Brownian motion as a fixed object in the image had a motion of 25 nm). Then, using a processor, the dose for which a distance range of bacterial cell motion is between 50 nm and 65 nm can be determined at a predetermined time of exposure, as for example, five minutes or more. This restriction in range of motion signals that the corresponding dose comprises the MBC.

The displacement associated with the Brownian motion of a freely moving bacterial cell in solution is given by $(2Dt)^{1/2}$ according to the diffusion model, 45 where D, the diffusion coefficient of bacteria, is ~10-5 cm$^2$/s and t is the time scale. For a time scale of 5-20 sec, this Brownian motion is several microns for free moving cell, much greater than the observed 65 nm for our cells attached to the surface. This discrepancy arises because the bacterial cells are attached to the surface in our case and their motion depends upon surface interactions.

While the loosely tethered cells showed a large decrease in the sub-μm motion upon antibiotic exposure, tightly bound cells displayed smaller motion changes (data not shown). A robust AST method must work for a bacterial population that contains a mixture of loosely and tightly bound cells. To demonstrate this capability, antibiotic effects on the "average distance" ($D_{AVG}$) were studied for a population of bacterial cells that included both tightly bound and partially bound cells. For this mixed population of bound cells, the $D_{AVG}$ was 265 nm (FIG. 3C) before the addition of polymyxin B and dropped to 123 nm at 10 min post-antibiotic exposure (FIG. 3D).

Referring now to FIG. 3D, average distance ($D_{AVG}$) of nine cells before and 10 min after the addition of polymyxin B (0.5 mg/ml) is shown. Plot 347 shows histogram bar 360 representing motion at time 0. Histogram bar 362 represents time at 10 minutes after introduction of the polymyxin B. Note that the displacement between time zero and time people to 10 minutes is substantially reduced from about 260 nm to about 110 nm.

Figures 4A, 4B, 4C, 4D, 4E, 4F:
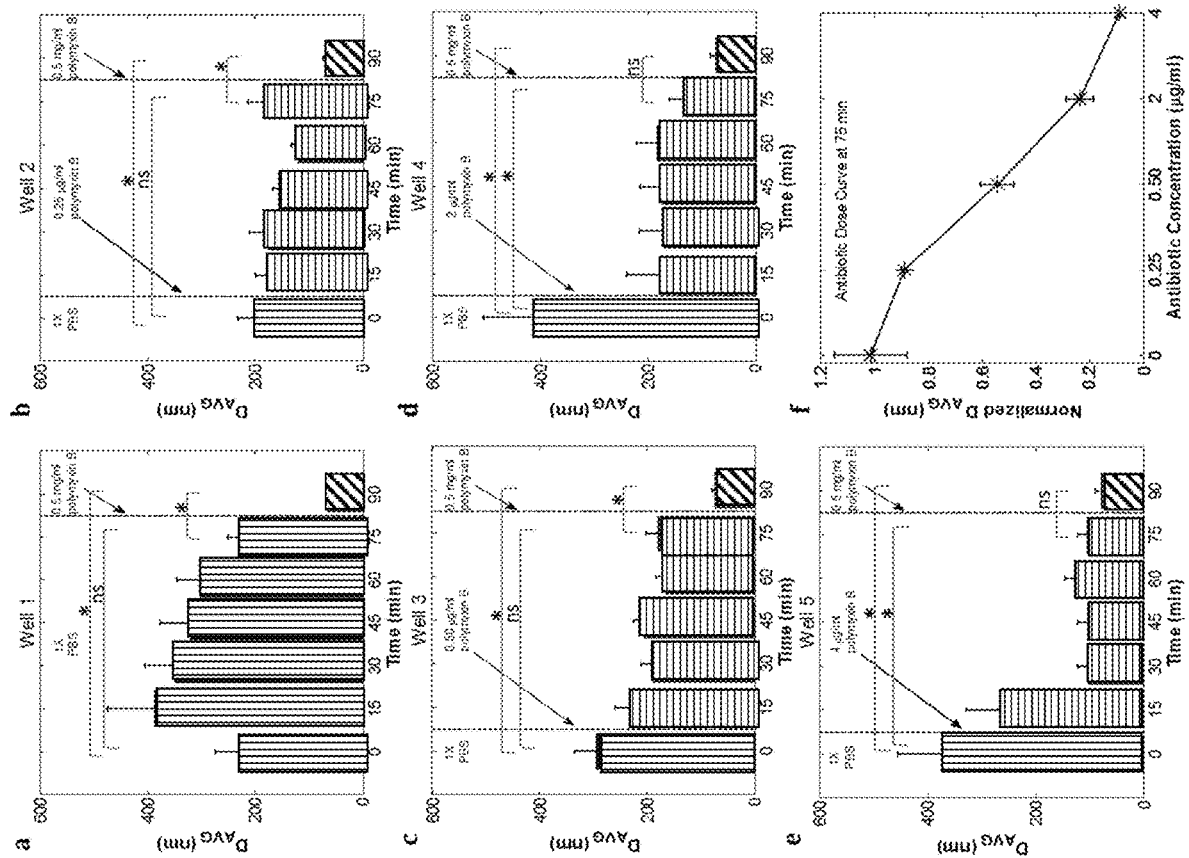
FIG. 4A-FIG. 4F illustrate plots of $D_{AVG}$ of a population of bacterial cells in different wells at different time points. Cells were sequentially exposed to 1×PBS (bar with vertical striping, baseline measurement), different clinically-relevant doses of polymyxin B (bars with horizontal striping, antibiotics added immediately after the baseline measurement), and a lethal dose of antibiotic (bars with diagonal striping, 0.5 mg/ml of polymyxin B added after the 75-min measurement).

Referring now jointly to FIG. 4A-FIG. 4E, $D_{AVG}$ of a population of bacterial cells in different wells at different time points is graphically shown. Cells were sequentially exposed to 1×PBS, different clinically-relevant doses of polymyxin B, and a lethal dose of antibiotic (0.5 mg/ml of polymyxin B added after the 75-min measurement). $D_{AVG}$ of cells in wells with 0 (FIG. 4A), 0.25 (FIG. 4B), 0.5 (FIG. 4C), 2 (FIG. 4D), and 4 μg/ml of polymyxin B (FIG. 4E).

To apply the above motion-tracking method to AST of the clinically relevant UPEC strain, UPEC cells were tethered to the glass surface via APTES surface chemistry and conjugation to the amine group of a bacterial surface protein. Antibiotic dose-dependent experiments were performed in a multiplexed format using multi-well slides and a 40× objective. First, baseline images were captured at 0 min for each well. Subsequently, polymyxin B at clinically relevant concentrations (4, 2, 0.5, and 0.25 μg/ml) was added to different wells, and images were recorded at 15 min intervals for 75 min. Finally, as a positive control, a bactericidal dose (0.5 mg/ml) of polymyxin B was added to all wells, and images were recorded after incubation for 15 min (at 90 min). The control well (Well 1) initially harbored 100 tethered cells (as described below with reference to FIG. 8A) with an initial $D_{AVG}$ of 228 nm (FIG. 4A). Over time (0-75 min), the number of cells on the surface increased gradually (as described below with reference to FIG. 8A) due to replication of the surface-tethered cells (as described below with respect to FIG. 9A-10B). During the first 15 min, $D_{AVG}$ increased from 228 nm to 388 nm, followed by a gradual decrease from 388 to 227 nm over 75 min (FIG. 4A). This decrease in $D_{AVG}$ in the absence of antibiotics may be attributed to the depletion of nutrients or adaptation of bacteria to the environment.46 In the presence of lethal polymyxin B concentration, $D_{AVG}$ decreased significantly from 227 nm to 64 nm in 75 min (FIG. 4A; p<0.05). $D_{AVG}$ vs. time was analyzed for polymyxin B varying between 0.5-4 μg/ml (FIG. 4B-FIG. 4E), showing clear correlation between the sub-μm motion and antibiotic concentration. Within this concentration range, the number of cells remained constant over 75 min (as described below with reference to FIG. 8A-FIG. 8E), indicating growth inhibition. At higher clinically relevant doses (e.g. 2 and 4 μg/mL), the $D_{AVG}$ value dropped post antibiotic addition, which shows the clear correlation between the sub-μm motion and antibiotic action. These findings validated that the sub-μm motion of surface-tethered UPEC cells with the APTES chemistry is correlated with the bacterial metabolic activity, thus enabling use for AST.

While the results described above are population-based analyses, this technology also allows for single cell analysis to provide fundamental phenotypic information for individual cells. For example, cells in the control well (without antibiotics) exhibited increased motion immediately after replication, followed by decreased motion after adding a lethal dose of polymyxin B (as described in more detail below with respect to FIG. 9A-10B). Another example is the observation of two phenotypic subpopulations detected upon exposure to low dose (0.25 μg/ml) polymyxin B. One subpopulation showed decreased motion (FIG. 4B) (as described in more detail below with respect to FIG. 11A-FIG. 11C), while the second subpopulation continued to replicate and showed increased motion with 0.25 μg/ml polymyxin B (as described in more detail below with respect to FIG. 12A-FIG. 12C). While analysis of different cells revealed large heterogeneity in cellular motion responses to low dose polymyxin B, at higher lethal polymyxin B concentration, all bacterial cells decreased motion (as described in more detail below with respect to FIG. 11A-FIG. 14B). These results showed that different cells in a sample may display different phenotypic and resistance responses for an antibiotic dose and that this single cell analysis capability allows detection of subpopulations of resistant bacteria in a sample.

Referring to FIG. 4F, an antibiotic dose curve of normalized $D_{AVG}$ at 75 min. is shown, where p<0.05; ns, means not significant. To obtain an antibiotic dose-response curve, the 75-min $D_{AVG}$ values were normalized between the 0-min $D_{AVG}$ values and the 90-min $D_{AVG}$ values as well as plotted against polymyxin B concentration, thus revealing decreased $D_{AVG}$ with increasing polymyxin B concentrations. At 4 μg/ml of polymyxin B, $D_{AVG}$ was similar to the $D_{AVG}$ of the lethal concentration (0.5 mg/ml) polymyxin B, indicating that 4 μg/ml polymyxin B is the minimum bactericidal concentration (MBC) at 75 min (referred to as MBC75 min). The polymyxin B minimum inhibitory concentration (MIC) was determined using the standard microdilution broth assay, thus revealing an MIC value of 1 µg/ml after 16 h incubation (as described in more detail below with respect to FIG. 15). Subsequent quantitative plating determined the standard incubation (16 h) MBC of 2 µg/ml (as described in more detail below with respect to FIG. 16). The MBC75 min value determined by this rapid AST method is lower than the MBC measured by the gold standard culturing method, but it is within the QC range of Clinical & Laboratory Standards Institute (CLSI), indicating that the present method can provide clinically-significant MBC values and perform rapid AST.

Referring now to FIG. 5A-5F, plots of $D_{AVG}$ of UPEC cells in human urine exposed to increasing concentrations of polymyxin B are there illustrated. UPEC cells (5×106 cfu/ml) were added to human urine samples, and $D_{AVG}$ was determined over time in the absence and presence of clinically-relevant concentrations of polymyxin B. The bars with vertical striping represent the baseline $D_{AVG}$ measurement of UPEC cells in urine. $D_{AVG}$ measurement of UPEC cells upon exposure to clinically-relevant concentrations of polymyxin B (bars with horizontal striping; antibiotics added immediately after the baseline measurement) and a high, bactericidal concentration of polymyxin B (bars with diagonal striping, 0.5 mg/ml added after the 90-min measurement). $D_{AVG}$ of cells in wells with (a) 0, (b) 0.25, (c) 1, (d) 2, (e) 4, and (f) 8 µg/ml of polymyxin B. *, $p<0.05$; ns, not significant.

Figures 5A, 5B, 5C, 5D, 5E, 5F:
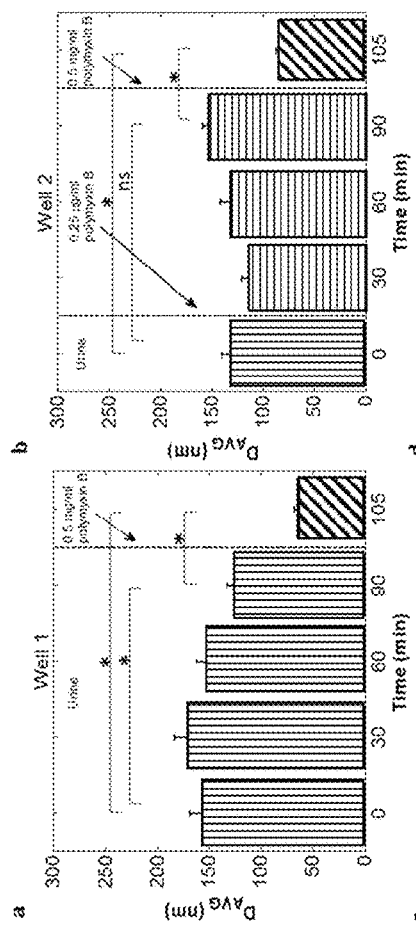
FIG. 5A-5F illustrate plots of $D_{AVG}$ of UPEC cells in human urine exposed to increasing concentrations of polymyxin B.

To test the feasibility of an example of a method for analyzing clinically relevant samples, urine samples collected from healthy patients were spiked with UPEC bacterial cells. Following surface tethering, images were recorded from six different wells with polymyxin B doses varying from 0 to 8 µg/ml. After 90 min incubation with 0.25, 1, or 2 µg/ml polymyxin B, $D_{AVG}$ either remained unchanged or increased over time (FIGS. 5b-d) compared to the urine samples without polymyxin B, indicating that the cells are viable and exhibit movement in urine samples with polymyxin B concentrations below 2 µg/ml (FIG. 5A). After adding a lethal dose (0.5 mg/ml) of polymyxin B, $D_{AVG}$ decreased significantly ($p<0.05$) within 15 min (FIG. 5A-5D). At clinically relevant concentrations of 4 and 8 µg/ml polymyxin B, $D_{AVG}$ decreased significantly ($p<0.05$) to $D_{AVG}$ values similar to the lethal (0.5 mg/ml) polymyxin B dose (FIG. 5E and FIG. 5F), revealing a polymyxin B MBC90 min of 8 µg/ml against UPEC in human urine samples.

By repeating these experiments with increasing concentrations of UPEC cells in urine samples, the polymyxin B MBC90 min was determined to be between 4 and 8 µg/ml (Table 1). These MBC data corroborated the previous experiments with 5×106 cfu/ml and standard culturing methods which proceeded for 16 h (see also FIG. 17A-FIG. 17F). These results further demonstrated the ability of the instant technique to perform rapid AST within 2 h for human urine samples.

TABLE 1

MBC of polymyxin B against UPEC cells in human urine samples.

| UPEC concentration in urine | Rapid AST MBC 90 min | Culture AST MBC (16 h) |
|---|---|---|
| 5 × 106 cfu/ml | 8 µg/ml | ND[a] |
| 107 cfu/ml | 4 µg/ml | ND[a] |
| 108 cfu/ml | 4 µg/ml | 2 µg/ml |

[a]ND not determined

Examples

Materials

Lyophilized pellets of *E. coli* O157:H7 (ATCC 43888) were purchased from Fisher Scientific and UPEC *E. coli* strain CFT073 was purchased from ATCC. Human urine samples, pooled from 20 healthy patients, were acquired from Bioreclamation IVT (Westbury, N.Y.) and stored at −80° C. (3-Aminopropyl) triethoxysilane (APTES) was purchased from Sigma-Aldrich (St. Louis, Mo.), aliquoted to smaller volumes under vacuum, and stored at 4° C. in a desiccator. Affinity-purified goat anti-*E. coli* O157: H7IgG polyclonal antibodies were purchased from Kirkegaard and Perry Laboratory Inc. (Gaithersburg, Md.). Stock solution of antibodies were prepared by dissolving in 1 ml PBS (1×) and stored in aliquots at −20° C. 1-Mercapto-11-undecyl hexa (ethylene glycol) (PEG) and carboxyl-terminated hexa(ethylene glycol) undecane thiol (PEG-COOH) were purchased from Nanoscience Instruments (Phoenix, Ariz.). Polymyxin B was purchased from Sigma-Aldrich, dissolved in 1×PBS at a stock concentration of 10 mg/ml, and stored in the dark at 2-8° C. according to manufacturer instructions. Other reagents were purchased from Sigma-Aldrich.

Growth and Preparation of Bacteria

The lyophilized *E. coli* O157:H7 bacteria were suspended in PBS and centrifuged at the speed of 50×g for 1 min to pellet the charcoal. The supernatant, containing bacteria, was collected and centrifuged at 2000×g for 15 min to pellet the bacteria. The bacterial pellet was resuspended in 1 ml of 1×PBS and mixed thoroughly. After 3 rounds of purification, the bacteria were resuspended in PBS with 5% glycerol and stored in 20 µl aliquots at −80° C. Similarly, *E. coli* strain CFT073 strain was cultured on solid Luria agar, suspended in PBS with 5% glycerol, and frozen in aliquots at −80° C.

An aliquot of frozen *E. coli* O157:H7 or *E. coli* CFT073 strain was thawed and used to inoculate 3 ml of Luria broth (LB) one day before the experiments. The overnight, saturated culture grown at 37° C. was diluted into fresh LB at a concentration of ~$10^7$ cfu/ml and grown at 37° C. with gentle rotary mixing until the cultures reached an $OD_{600}$ of 0.56, indicating the mid-logarithmic phase of growth. The corresponding concentration of the bacteria was 4.67×$10^8$ cfu/ml. Bacterial cells were collected by centrifugation at 2000×g for 15 min and resuspended in 1 ml PBS (1×) to an OD of 0.56. For urine experiments, pooled urine samples were sterilized via passage through a 0.2 µm filter and inoculated with freshly cultured UPEC cells to the desired concentration.

Sensor Chip Surface Functionalization

Clean BK7 glass coverslips were coated with 1.5 nm chromium and 48 nm gold and used as sensing chips. The chips were rinsed with deionized water and ethanol multiple times followed by drying with nitrogen gas and cleaning with a hydrogen flame. For antibody surface, the cleaned chips were submerged in 1 mM PEG/PEG-COOH ethanol solution and left in the dark for 24 h to coat a PEG/PEG-COOH self-assembled monolayer (SAM) on each chip. The PEG/PEG-COOH SAM-coated chips were activated with 500 µl of a freshly prepared mixture of 0.1 M NHS and 0.4M EDC in 1:1 ratio to produce NHS ester receptors, which react with the primary amine groups on the antibodies via an amide bond. Chips with activated PEG/PEG-COOH SAM were cleaned with deionized water and blown dry with nitrogen gas. Polyclonal anti-*E. coli* O157:H7 IgG antibodies dissolved in 20 mM sodium acetate, pH 5.5 at a concentration of 30 µg/ml were immediately applied to the NHS/EDC-activated surfaces and incubated for 30 min. The antibody-coated chips were again cleaned with deionized water and dried with nitrogen gas prior to bacterial cell capture and imaging.

For the APTES surface, 22×60 mm BK7 glass slides from VWR (Radnor, Pa.) were used. The glass slides were thoroughly cleaned with deionized water and ethanol and dried with nitrogen gas. The glass slide was activated with freshly prepared 1% APTES in 95% ethanol for 15 sec. to attach the APTES linker to the sensor surface. The APTES linked sensor chips were again cleaned with ethanol and dried with nitrogen gas prior to bacterial cell capture on the imaging setup. A black permanent marker spot was placed beneath the coated surface of the glass slide for alignment purposes. A reusable, self-adhering multi-well FlexiPERM (Sarstedt) attachment was affixed to the top of the slide.

Bacterial Immobilization

*E. coli* O157:H7 cells (20 µl) were added to antibody-coated sensor chips containing 500 µl PBS (1×). Cells were tethered onto the sensor surface after 10-15 min incubation at room temperature. Chips were washed with PBS buffer to remove untethered bacterial cells. During incubation in LB at room temperature, tethered bacterial cells were observed elongating, indicating that the tethered cells were viable and metabolically active.

UPEC cells suspended in urine or 1×PBS were added to the APTES coated slides with attached FlexiPERM multi-wells. Cells were tethered to the surface after 10-15 min incubation at room temperature, and unattached bacterial cells were removed by washing the chips with PBS.

Drug Perfusion System

A gravity-based multichannel drug perfusion system (Warner Instrument, Hamden, Conn.) was used to deliver medium and buffers to sensor chip wells. Sample solutions flowed at a rate of 330 µl/min with the transition time between different solutions in the range of 1-2 sec. The flow system was stopped and stabilized for 5 min before recording videos. Antibiotics were manually pipetted into the wells for all UPEC experiments.

Imaging Setup

The imaging setup consisted of an inverted microscope (Olympus IX-70) (FIG. 1).[50-52] A 60× oil immersion objective with a numerical aperture (NA) of 1.49 or a 40× objective (NA 0.75) was used to perform the experiments. The glass slides were placed on a motorized microscope stage (BioPrecision2 X-Y Stage, Ludl Electronic Products Ltd., Hawthorne, N.Y.) above the objective lens. A top mounted white light source was used to illuminate the sample and a CCD (Pike-032B, Allied Vision Technologies, Newburyport, Mass.) or a CMOS camera (GS3-U3-23S6M-C, Point Grey Research, Richmond, BC, Canada) was used to record images. The assembled glass chip with an attached FlexiPERM well was then mounted onto the microscope stage. Light intensity was adjusted to obtain the best image contrast without image saturation.

Image Collection and Processing

Images were recorded and converted into binary images using segmentation algorithms previously developed[53] and described in further detail below with respect to FIG. 6A-FIG. 6D.

Broth Microdilution Assay

Broth microdilution assay was used to determine the polymyxin B MIC and MBC following a standard protocol.[54] Exponential phase UPEC CFT073 cultures were grown as described above, and bacterial suspensions ($1 \times 10^8$ cfu/ml) were prepared in Mueller Hinton broth. Bacterial suspensions (100 µl of $5 \times 10^6$, $10^7$, or $10^8$ cfu/ml) were added to wells of 96-well microtiter plates containing polymyxin B (0.125-8 µg/ml). The MIC was determined by measuring the absorbance at 600 nm after 16 h standing incubation at 37° C. Cell viability and MBC values were determined by plating duplicate 10-fold serial dilutions for each sample onto Luria Broth agar plates and enumerating colonies after 16 h incubation at 37° C. The MBC value was determined as the minimum antibiotic concentration that failed to yield any positive bacterial cultures.

Statistical Analysis

Paired student t-tests were used to analyze statistical differences between different values (see FIG. 3A-FIG. 3D). Repeated measures one-way ANOVA and Games-Howell post hoc test were used to assess statistical significance between different time points (see FIG. 4A-FIG. 5F). Custom MATLAB scripts were generated to perform statistical analysis.

Detailed Image Collection and Processing Steps for Quantification of Bacterial Cells Displacement Referring now to FIG. 6A-FIG. 6D, an example image processing of bacterial cells to quantitate X and Y displacement and movement is shown. FIG. 6A shows an example of an image (greyscale image) of a bacterial cell captured using the imaging setup. FIG. 6B shows an example where the greyscale image of a bacterial cell is converted into a binary image with the superimposed center of the cell 603. FIG. 6C shows an example where the center of the cell is plotted over 20 sec. of video to obtain the displacement, and thus movement, of the cell. Scale bar 601 is 1 µm.

All *E. coli* O157:H7 experiment image sequences were collected at 106 fps at a pixel resolution of 640×480 using the Pike-032B CCD camera. All uropathogenic *E. coli* (UPEC) experiment image sequences were collected at 26.6 fps at a pixel resolution of 1920×1200 via the PointGrey CMOS camera. The stage was translated to each well sequentially at the marker spot area and recorded 5 sec image sequences for each well. This process was repeated every 15 min across multiple time points. The microscope focus was set to image bright bacterial cells with darker backgrounds in the greyscale mode. All images were processed using MATLAB programs and ImageJ scripts.

Greyscale images were converted into binary images using a MATLAB script. In the greyscale images, the focus of the microscope has been adjusted so that the bacterial cells were brighter (higher pixel intensities) compared to the background region. For every greyscale image (FIG. 6A), a unimodal histogram of pixel intensities was plotted (FIG. 6B). From the histogram of pixel intensities (FIG. 6B), a threshold (T) value was then determined at the point of drop in the intensity histogram towards the higher pixel intensity tail (right side in FIG. 6B). All pixel intensities greater than the threshold value T were converted to 1, while all the pixel intensities lower than T were converted to 0. The binary images segmented the bacterial cells from the background. Standard morphological operations were performed on the binary images to improve the segmentations, including removing spur points, breaking H-connected sections, and filling holes. The greyscale images were thus converted into binary images with segmented bacterial cells distinct from the background (FIG. 6C).

To quantify bacterial motion, region props MATLAB command was used to obtain the "Centroid" 603 for each segmented cell in the binary images. The centroid is the X and Y coordinates of the bacterial cell center and is calculated as the mean of all non-zero pixels which the bacterial cell occupies. Next tracked the cell motion was tracked over 20 sec. for E. coli O157:H7 experiments and 5 sec. for UPEC experiments by determining the centroid of each segmented cell in the image sequence. To ensure proper tracking of individual cell movement, the center of the bacterium in each image was compared to the previous frame to ensure that the movement of centroids is within the cell length. Finally, the motion of the bacteria was plotted as the X and Y displacement of the center (FIG. 6D). The algorithms also counted the total cells tracked as the measure of total cells in the well.

The X and Y displacement of the cell center was calculated by subtracting the X and Y coordinates of an individual cell from the cell's average position over the length of the image sequences. The "Distance" moved by the center of a bacterial cell was calculated by using the formula Distance= $\sqrt{\sigma x^2 + \sigma y^2}$, where $\sigma x$ and $\sigma y$ represents the standard deviation of X and Y displacement, respectively. In addition, $D_{AVG}$, the average distance for a population of cells in an image sequence was calculated as the mean value of all individual cell distances.

Figure 7A:
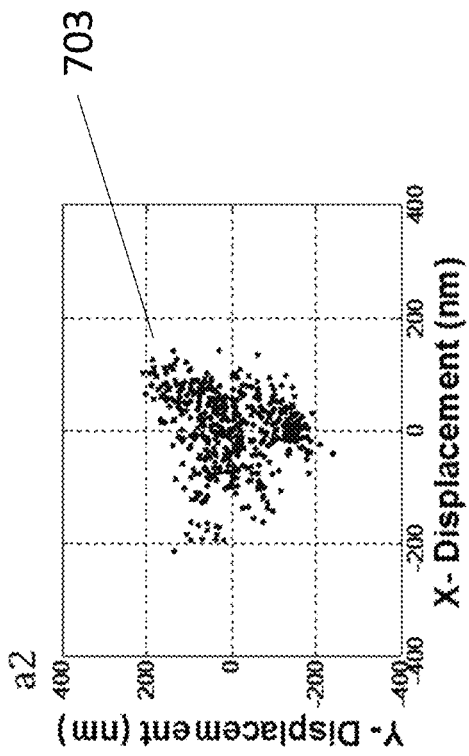
FIG. 7A-FIG. 7D show an example of motion (X and Y displacement) of a live bacterial cell compared to a fixed marker spot.
Figure 7B:
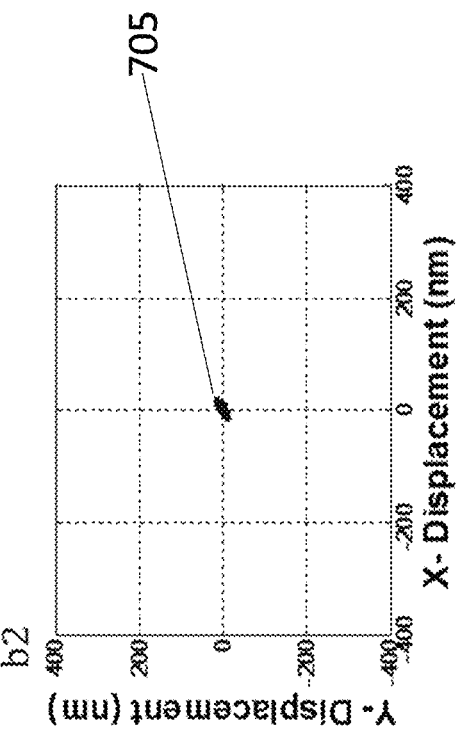

Referring now to, FIG. 7A-FIG. 7D an example of motion (X and Y displacement) of a live bacterial cell compared to a fixed marker spot is shown. In particular, FIG. 7A shows an image of a partially tethered bacterial cell captured using the imaging setup with superimposed displacement of the center shown via dots 703. Magnification and quantitation of the displacement of the cell center over 20 sec., revealing a range of a few hundred nanometers (FIG. 7B).

Figure 7C:
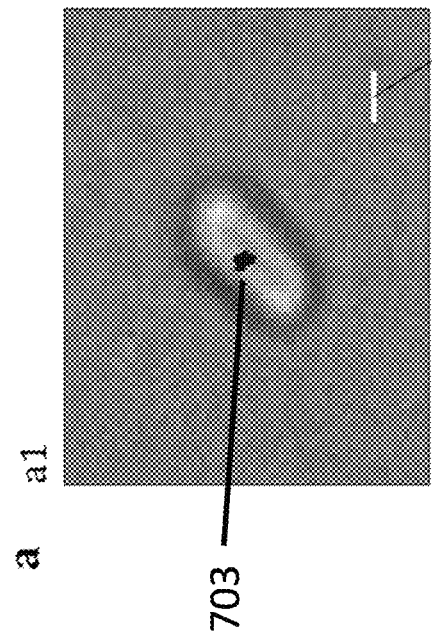
Figure 7D:
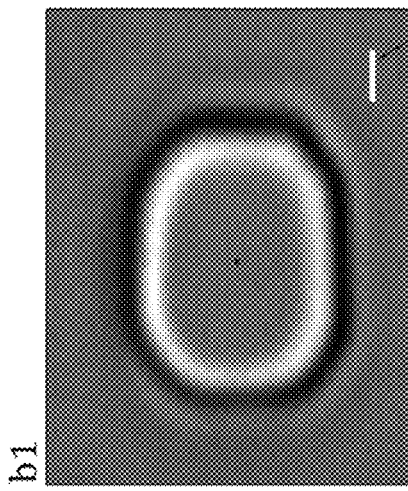

FIG. 7C shows an image of a fixed marker spot captured using the imaging setup with superimposed displacement of center shown via dots 705 (as best shown in FIG. 7D). Magnification and quantitation of the displacement of the center of the marker spot over 20 sec, indicating that the measurement noise level is −25 nm. Scale bar 701=1 μm.

Referring now to FIG. 8A-FIG. 8E, examples of dose dependency of a total number of UPEC cells in the images are shown. Total number of bacterial cells counted by an image processing algorithm in images captured from multiple wells at different time points. Cells were sequentially exposed to 1×PBS where bars with vertical striping each represent a baseline measurement. Different clinically-relevant doses of polymyxin B (bars with horizontal striping, antibiotics added immediately after the baseline measurement), and a lethal dose of antibiotic (bars with diagonal striping, 0.5 mg/ml added after the 75 mins measurement). Polymyxin B concentrations: (a) 0, (b) 0.25, (c) 0.5, (d) 2, and (e) 4 μg/ml.

Referring now to FIG. 9A-FIG. 9C, changes in sub-μm motion of a replicating UPEC cell partially tethered on the glass surface are shown. FIG. 9A shows images of a dividing UPEC bacterial cell with superimposed center displacement over time in 1×PBS (FIG. 9A, panels a1-a3) and after addition of 0.5 mg/ml polymyxin B before T=90 min (FIG. 9A, panel a4). FIG. 9B shows magnified plots (FIG. 9B, panels b1-b4) of the center displacements shown in FIG. 9A panels a1-a4. FIG. 9C illustrates where displacement distance showed an increase as the cell replicates (FIG. 9A panel a3) into two daughter cells 903, 904 and a subsequent decrease after adding a lethal dose of polymyxin B (0.5 mg/ml) (bars with diagonal striping). Scale bars are the same in each of the FIG. 9A panels and are equal to 1 μm.

FIG. 10A-FIG. 10C illustrate changes in sub-μm motion of a replicating UPEC cell partially tethered on the glass surface. Images of a dividing UPEC bacterial cell with superimposed center displacement over time in 1×PBS (FIG. 10A, panels a1-a3) and after addition of 0.5 mg/ml polymyxin B over time in 1×PBS (FIG. 10A, panels a1-a3) and after addition of 0.5 mg/ml polymyxin B before T=90 min (FIG. 10A, panel a4).

Referring more specifically now to FIG. 10B, there shown are magnified plots (FIG. 10B, panels b1-b4) of the center displacements shown in FIG. 10A, panels a1-a4. Referring more specifically now to FIG. 10C, there shown is an illustration of how displacement distance increased after 30 min as the cell elongates and replicates (as shown in FIG. 10A panel a2) and subsequently decreased after one daughter cell failed to tether onto the glass surface at 60 min. Displacement distance was further decreased after adding lethal a lethal dose of polymyxin B (0.5 mg/ml) (bars with diagonal striping). As above, the scale bars shown in the lower right-hand corner of the images equal 1 μm.

Referring now to FIG. 11A-FIG. 11C illustrate a decrease in sub-μm motion of surface-tethered UPEC cells exposed to 0.25 μg/ml polymyxin B. FIG. 11A shows images of two individual UPEC bacterial cells with superimposed center displacement over time in 1×PBS (FIG. 11A, panel a1) and after addition of 0.25 μg/ml (FIG. 11A, panels a2 and a3) or 0.5 mg/ml (FIG. 11A, panel a4) of polymyxin B. FIG. 11B-FIG. 11C show displacement distance of the UPEC cell at different time points. The cell exhibited distance decreases at 30 and 60 min after adding 0.25 μg/ml of polymyxin B (bars with horizontal striping). This cell is representative of subpopulation 1, whereby low dosage of polymyxin B decreased the $D_{AVG}$ of the population. The distance further decreased (bars with diagonal striping) after adding a lethal dosage (0.5 mg/ml) of polymyxin B. As above, the scale bars shown in the lower right-hand corner of the images equal 1 μm.

Figure 12A:
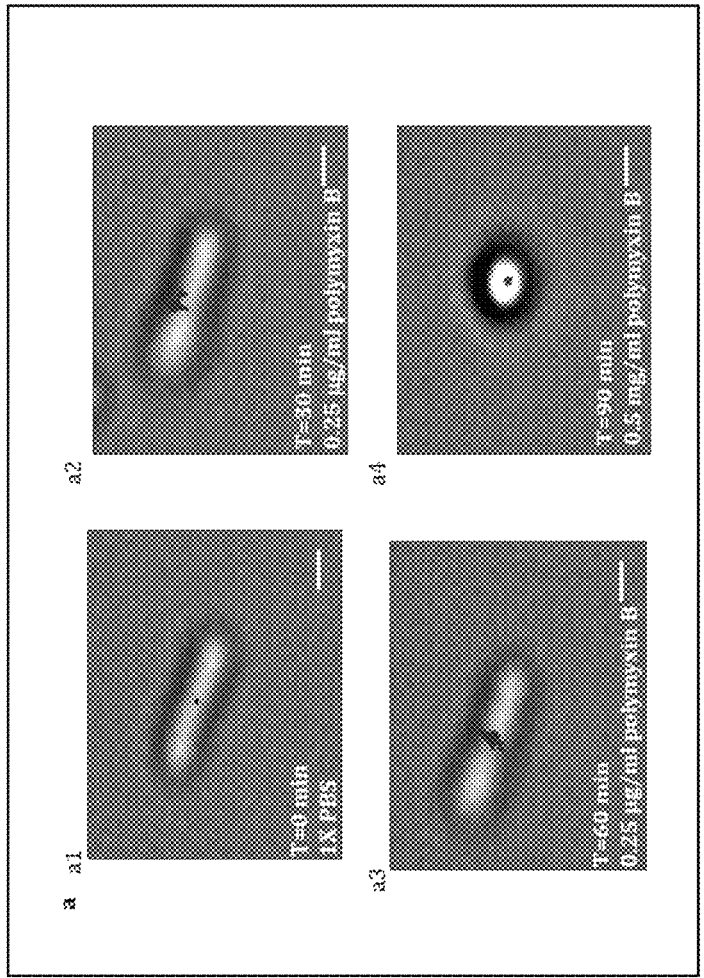
FIG. 12A illustrates images of an increase in sub-μm motion of a surface-tethered UPEC cell exposed to 0.25 μg/ml polymyxin B over time.
Figure 12B:
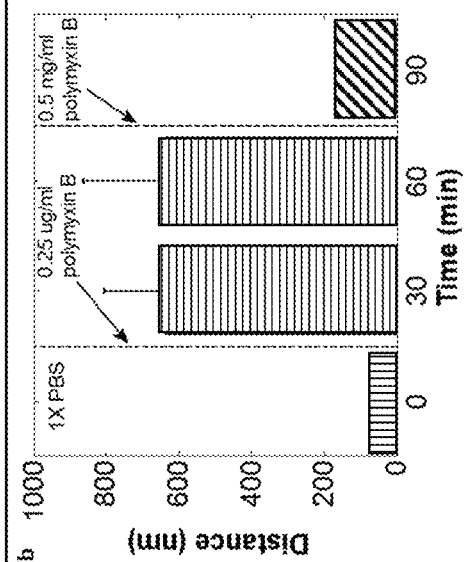
FIG. 12B plots displacement distance of the cell of FIG. 12A at different time points.

Referring now to, FIG. 12A images of an increase in sub-μm motion of a surface-tethered UPEC cell exposed to 0.25 μg/ml polymyxin B over time are illustrated. Images of an individual UPEC bacterial cell with superimposed center over time in 1×PBS (FIG. 12A, panel a1) and after addition of 0.25 μg/ml (FIG. 12A, panels a2 and a3) or 0.5 mg/ml (FIG. 12A, panel a4) of polymyxin B are shown. As above, the scale bars shown in the lower right-hand corner of the images equal 1 μm. FIG. 12B plots displacement distance of the cell of FIG. 12A at different time points. Displacement distance of the cell as shown at different time points. The cell showed a consistent distance increase at 30 and 60 min after adding 0.25 μg/ml of polymyxin B (bars with horizontal striping). This cell is representative of subpopulation 2, which exhibited motion increases after the addition of a low concentration of polymyxin B. Distance decreased (bars with diagonal striping) after adding a lethal dosage (0.5 mg/ml) of polymyxin B, thus validating the metabolic origins of the motion.

Figure 13A:
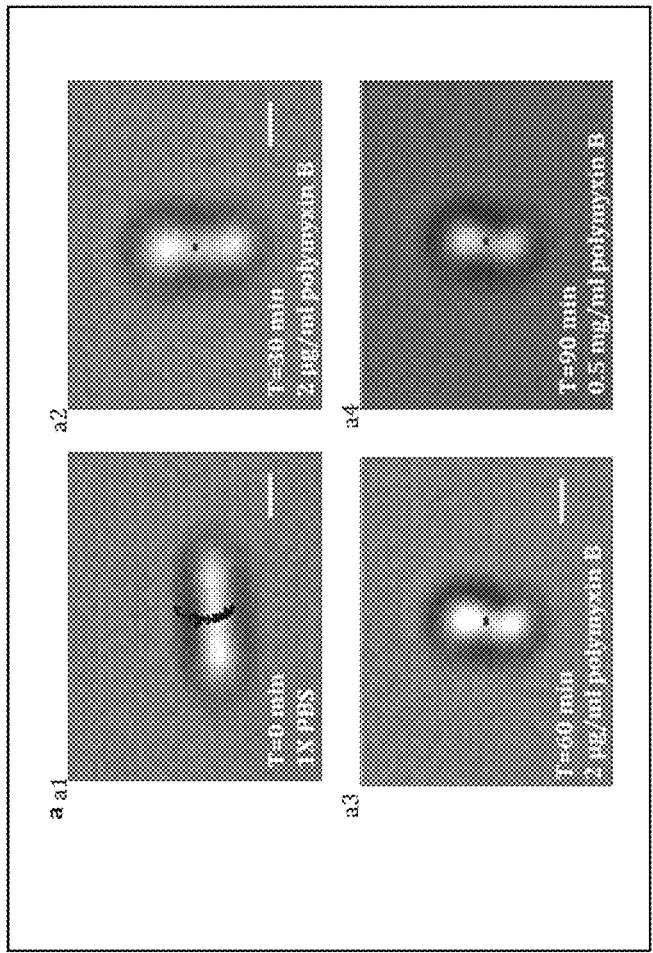
FIG. 13A illustrates images of cells showing a decrease in sub-μm motion of a surface-tethered UPEC cell exposed to 2 μg/ml polymyxin B over time.

FIG. 13A illustrates images of cells showing a decrease in sub-μm motion of a surface-tethered UPEC cell exposed to 2 μg/ml polymyxin B over time. Images of a UPEC bacterial cell with superimposed motion over time in 1×PBS (FIG. 13A, panel a1) and after addition of 2 μg/ml (FIG. 13A, panels a2 and a3) or 0.5 mg/ml (FIG. 13A, panel a4) of polymyxin B. As above, the scale bars shown in the lower right-hand corner of the images equal 1 µm.

Figure 13B:
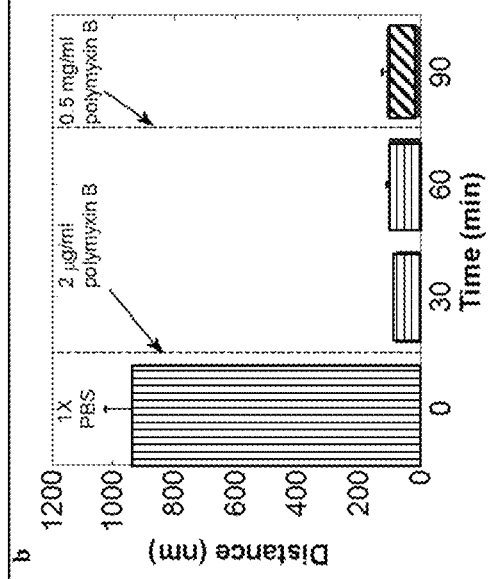
FIG. 13B plots displacement distance of the cell of FIG. 13A at different time points.

FIG. 13B plots displacement distance of the cell of FIG. 13A at different time points. Displacement distance of the cell at different time points. Cells exhibited distance decreases at 30 and 60 min after adding 2 µg/ml polymyxin B (bars with horizontal striping). The decreased distance is similar in scale to the distance after adding the bactericidal concentration of 0.5 mg/ml polymyxin B (bars with diagonal striping), indicating cellular death after adding 2 µg/ml polymyxin B.

Figure 14A:
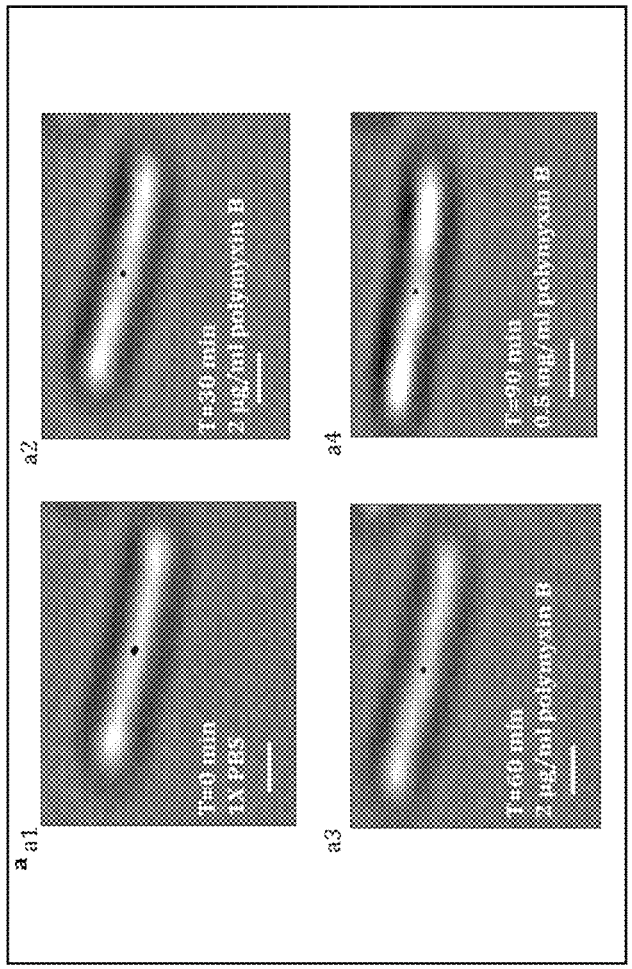
FIG. 14A illustrates images of cells showing a decrease in sub-μm motion of a surface-tethered UPEC cell exposed to 2 μg/ml polymyxin B over time.

Referring now to FIG. 14A, images of cells showing a decrease in sub-µm motion of a surface-tethered UPEC cell exposed to 2 µg/ml polymyxin B over time are illustrated. Images of an individual UPEC bacterial cell with superimposed motion over time in 1×PBS (FIG. 14A, panel a1) and after addition of 2 µg/ml (FIG. 14A, panels a2 and a3) and 0.5 mg/ml polymyxin B (FIG. 14A, panel a4). As above, the scale bars shown in the lower right-hand corner of the images equal 1 µm.

Figure 14B:
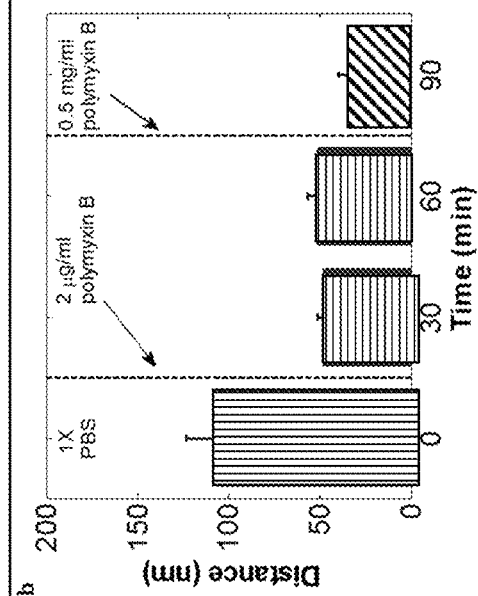
FIG. 14B plots displacement distance of the cell of FIG. 14A at different time points.

Referring now to FIG. 14B, displacement distance of the cell of FIG. 14A at different time points is plotted. Cells exhibited distance decreases at 30 and 60 min after adding 2 µg/ml polymyxin B (bars with horizontal striping). Displacement distance of the cell at different time points. Cells exhibited distance decreases at 30 and 60 min after adding 2 µg/ml polymyxin B (bars with horizontal striping). The distance was further decreased after adding the bactericidal concentration of 0.5 mg/ml polymyxin B (bars with diagonal striping). This result indicates that this individual cell is viable, but is exhibiting decreased motion after adding 2 µg/ml polymyxin B.

Figure 15:
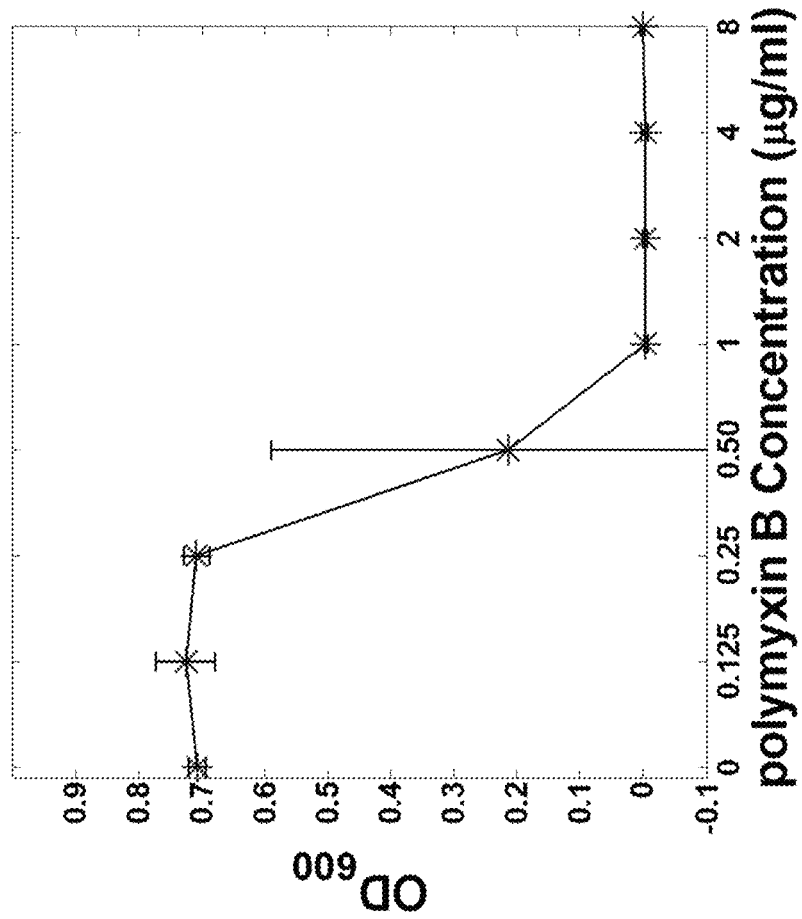
FIG. 15 shows a plot measuring inhibition of UPEC in Mueller Hinton broth (MHB) after incubation with increasing polymyxin B concentrations.

Referring now to FIG. 15, a plot measuring inhibition of UPEC in Mueller Hinton broth (MHB) after incubation with increasing polymyxin B concentrations is shown. Growth inhibition of UPEC in Mueller Hinton broth (MHB) after incubation with increasing polymyxin B concentrations. UPEC cells ($5 \times 10^6$/ml) were incubated in MHB for 16 h at 37° C., followed by optical density measurements ($OD_{600}$). Average and standard deviation $OD_{600}$ measurements collected from triplicate experiments were plotted.

Referring now to FIG. 16, a table illustrating growth inhibition and bactericidal activity of the antibiotic polymyxin B is shown. After determining growth inhibition after 16 h incubation at 37° C., 5 µl of each culture was spotted onto Luria agar and incubated for 16 h at 37° C. to enumerate cfu. Data represent results from three independent experiments.

Referring now to FIG. 17A-FIG. 17F plots of bactericidal activity of polymyxin B against UPEC in spiked urine samples are shown. UPEC cells were added to human urine samples and exposed to different polymyxin B concentrations. At indicated times, 5 µl of each suspension was inoculated onto Luria agar. After incubation at 37° C. for 16 h, colonies were enumerated and recorded as cfu/ml. The bars with vertical striping represent the initial cfu/ml of UPEC cells in urine, and bars with horizontal striping represent cfu/ml of UPEC cells upon exposure to clinically-relevant concentrations of polymyxin B (antibiotics added immediately after the baseline measurement) in urine. After addition of a high, bactericidal concentration of polymyxin B (0.5 mg/ml added after the 90-min measurement) and an additional 15-min incubation, no colonies were detected on Luria agar. These results indicated that the polymyxin B MBC against UPEC cells spiked in human urine was of 2 µg/ml.

Figure 18A:
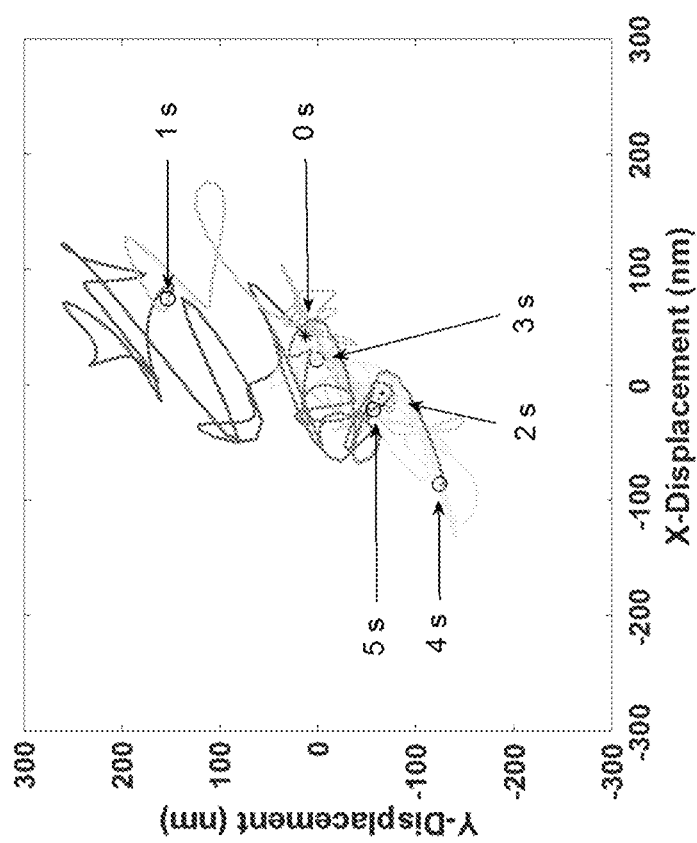
FIG. 18A shows motion of a living bacterial cell over time is shown.

Referring now to FIG. 18A, motion of a living bacterial cell over time is shown: FIG. 18A shows displacement of an alive bacterial cell over 5 s in 1×PBS. The position of the bacterial cell at 0 s (marked by *) and various other time points (marked by o) is shown.

Figure 19A:
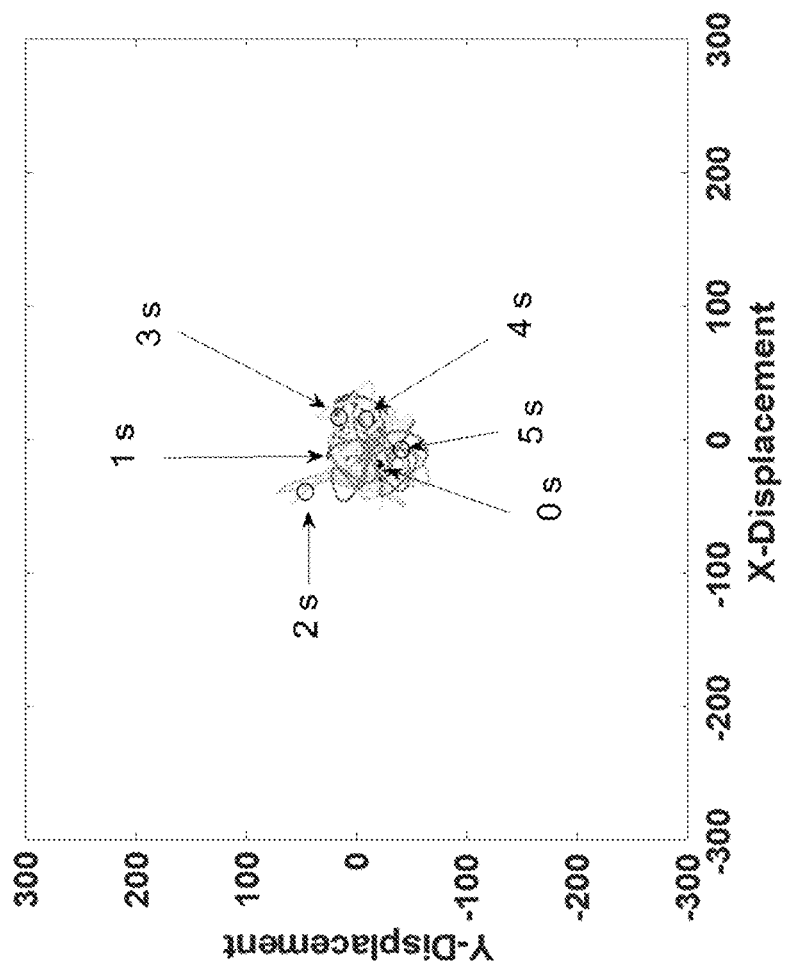
FIG. 19A and FIG. 19B show motion of a dead bacterial cell over time.
Figure 19B:
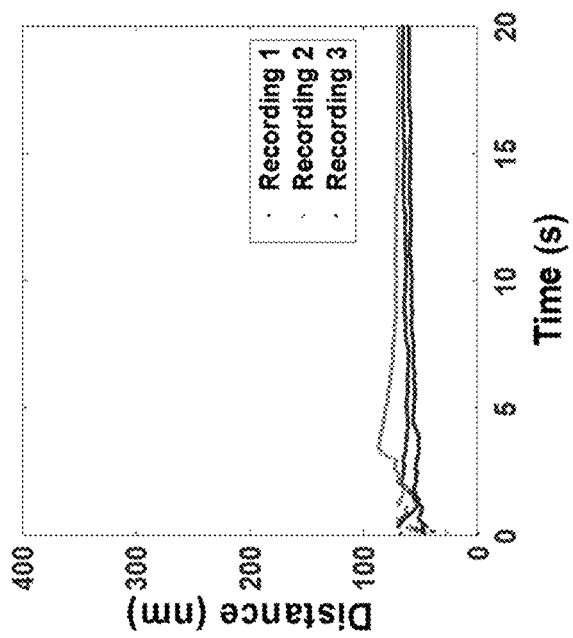

Referring now to FIG. 19A and FIG. 19B, motion of a dead bacterial cell over time. (a) Displacement of a dead bacterial cell over 5 s in 1×PBS. The position of the bacterial cell at 0 s (marked by *) and various other time points (marked by o) is shown. (b) Distance of a dead bacterium after 5 mins in 0.5 mg/ml polymyxinB over triplicate 20 s recordings. At 20 s, the distance from triplicates is averaged to obtain motion of the cell at 5 mins in 0.5 mg/ml polymyxin B.

Figure 20A:
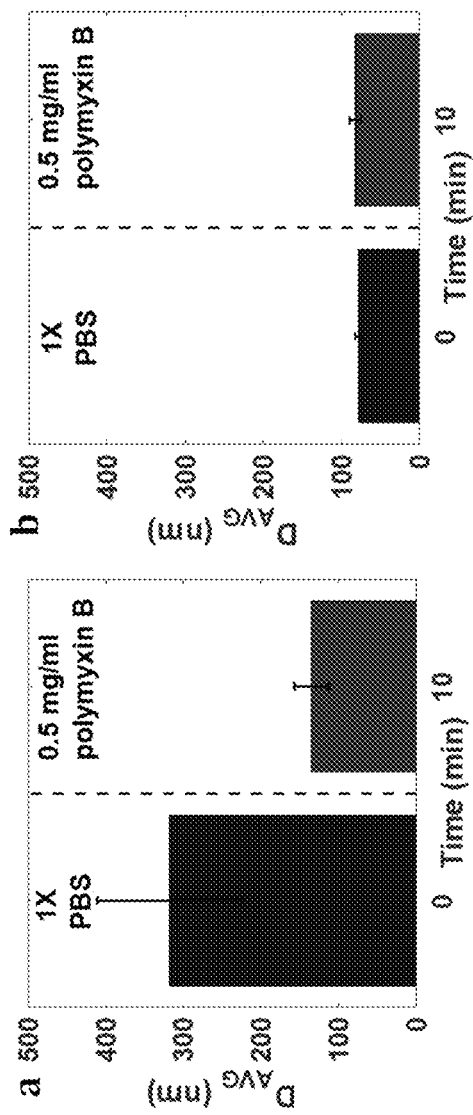
Figure 20C:
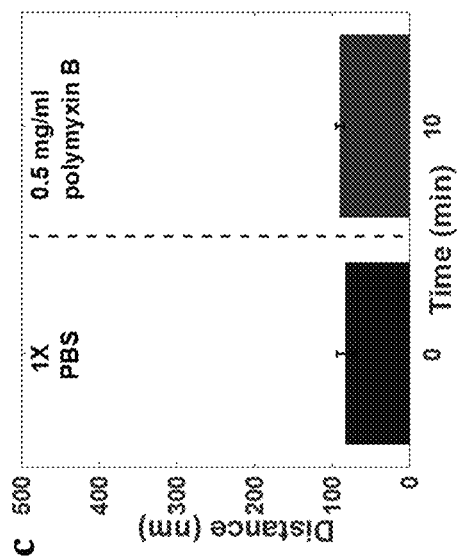

Referring now to FIG. 20A-FIG. 20C, motion changes of loosely and completely tethered bacterial cells (a) $D_{AVG}$ of loosely tethered bacterial cells shows a significant decrease after addition of 0.5 mg/ml polymyxin B. (b) $D_{AVG}$ of completely tethered bacterial cells show no change after addition of 0.5 mg/ml polymyxin B. (c) A completely tethered alive bacterium in 1×PBS shows no changes in distance after 10 mins in 0.5 mg/ml polymyxin B.

Certain exemplary embodiments of the invention have been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

As another example, measuring sub-µm motion changes of loosely bound microorganisms after they interact with antibiotics correspond to a measure of their susceptibility to antibiotics, leading to a new and rapid way to perform Antibiotic Susceptibility Test (AST), a critical diagnostic test currently. Antibiotic susceptibility information for single bacterial cells (single cell antibiotic susceptibility) is provided using the above invention, which is not possible using current assays which measure bulk populations. Single cell susceptibility analysis can also be used for clinical cases of polymicrobial infections and to identify resistant cells in a population, which is not possible using current bulk assays.

REFERENCES

The teachings of the following publications are incorporated herein in their entirety by this reference.
(1) Daniels, R. Surviving the First Hours in Sepsis: Getting the Basics Right (an Intensivist's Perspective). *J. Antimicrob. Chemother.* 2011, 66, 11-23.
(2) Barenfanger, J.; Drake, C.; Kacich, G. Clinical and Financial Benefits of Rapid Bacterial Identification and Antimicrobial Susceptibility Testing. *J. Clin. Microbiol.* 1999, 37, 1415-1418.
(3) Kumar, A.; Roberts, D.; Wood, K. E.; Light, B.; Parrillo, J. E.; Sharma, S.; Suppes, R.; Feinstein, D.; Zanotti, S.; Taiberg, L.; et al. Duration of Hypotension before Initiation of Effective Antimicrobial Therapy Is the Critical Determinant of Survival in Human Septic Shock*. 2006, 34, 1589-1596.
(4) Zurek, L.; Ghosh, A. Insects Represent a Link between Food Animal Farms and the Urban Environment for Antibiotic Resistance Traits. *Appl. Environ. Microbiol.* 2014, 80, 3562-3567.

(5) Laxminarayan, R.; Duse, A.; Wattal, C.; Zaidi, A. K. M.; Wertheim, H. F. L.; Sumpradit, N.; Vlieghe, E.; Hara, G. L.; Gould, I. M.; Goossens, H.; et al. Antibiotic Resistance—the Need for Global Solutions. *Lancet Infect. Dis.* 2013, 3099, 1057-1098.

(6) Jorgensen, J. H.; Ferraro, M. J. Antimicrobial Susceptibility Testing: A Review of General Principles and Contemporary Practices. *Clin. Infect. Dis.* 2009, 7750, 1749-1755.

(7) Jorgensen, J. H.; Ferraro, M. J. Antimicrobial Susceptibility Testing: A Review of General Principles and Contemporary Practices. *Clin. Infect. Dis.* 2009, 49, 1749-1755.

(8) Syal, K.; Mo, M.; Yu, H.; Iriya, R.; Jing, W.; Guodong, S.; Wang, S.; Grys, T. E.; Haydel, S. E.; Tao, N. Current and Emerging Techniques for Antibiotic Susceptibility Tests. *Theranostics* 2017, 7, 1795-1805.

(9) Van Boeckel, T. P.; Gandra, S.; Ashok, A.; Caudron, Q.; Grenfell, B. T.; Levin, S. A.; Laxminarayan, R. Global Antibiotic Consumption 2000 to 2010: An Analysis of National Pharmaceutical Sales Data. *Lancet Infect. Dis.* 2014, 14, 742-750.

(10) Humphries, R. M.; Hindler, J. A. Emerging Resistance, New Antimicrobial Agents . . . but No Tests! The Challenge of Antimicrobial Susceptibility Testing in the Current Us Regulatory Landscape. *Clin. Infect. Dis.* 2016, 63, 83-88.

(11) Sin, M. L. Y.; Mach, K. E.; Wong, P. K.; Liao, J. C. Advances and Challenges in Biosensor-Based Diagnosis of Infectious Diseases. *Expert Rev. Mol. Diagn.* 2014, 14, 225-244.

(12) Bauer, K. A.; Perez, K. K.; Forrest, G. N.; Goff, D. A. Review of Rapid Diagnostic Tests Used by Antimicrobial Stewardship Programs. *Clin. Infect. Dis.* 2014, 59, S134-S145.

(13) Price, C. S.; Kon, S. E.; Metzger, S. Rapid Antibiotic Susceptibility Phenotypic Characterization of *Staphylococcus Aureus* Using Automated Microscopy of Small Numbers of Cells. *J. Microbiol. Methods* 2014, 98, 50-58.

(14) Mohan, R.; Sanpitakseree, C.; Desai, A. V.; Sevgen, S. E.; Schroeder, C. M.; Kenis, P. J. A. A Microfluidic Approach to Study the Effect of Bacterial Interactions on Antimicrobial Susceptibility in Polymicrobial Cultures. *RSC Adv.* 2015, 5, 35211-35223.

(15) Choi, J.; Jung, Y.-G.; Kim, J.; Kim, S.; Jung, U.; Na, H.; Kwon, S. Rapid Antibiotic Susceptibility Testing by Tracking Single Cell Growth in a Microfluidic Agarose Channel System. *Lab Chip* 2012, 13, 280-287.

(16) Sinn, I.; Albertson, T.; Kinnunen, P.; Breslauer, D. N.; McNaughton, B. H.; Burns, M. a; Kopelman, R. Asynchronous Magnetic Bead Rotation Microviscometer for Rapid, Sensitive, and Label-Free Studies of Bacterial Growth and Drug Sensitivity. *Anal. Chem.* 2012, 84, 5250-5256.

(17) Choi, J.; Yoo, J.; Lee, M.; Kim, E.-G.; Lee, J. S.; Lee, S.; Joo, S.; Song, S. H.; Kim, E.-C.; Lee, J. C.; et al. A Rapid Antimicrobial Susceptibility Test Based on Single-Cell Morphological Analysis. *Sci. Transl. Med.* 2014, 6, 267ra174.

(18) MacH, K. E.; Mohan, R.; Baron, E. J.; Shih, M. C.; Gau, V.; Wong, P. K.; Liao, J. C. A Biosensor Platform for Rapid Antimicrobial Susceptibility Testing Directly from Clinical Samples. *J. Urol.* 2011, 185, 148-153.

(19) Mohan, R.; Mach, K. E.; Bercovici, M.; Pan, Y.; Dhulipala, L.; Wong, P. K.; Liao, J. C. Clinical Validation of Integrated Nucleic Acid and Protein Detection on an Electrochemical Biosensor Array for Urinary Tract Infection Diagnosis. *PLoS One* 2011, 6, e26846.

(20) Rolain, J. M.; Mallet, M. N.; Fournier, P. E.; Raoult, D. Real-Time PCR for Universal Antibiotic Susceptibility Testing. *J Antimicrob Chemother.* 2004, 54, 538-541.

(21) Ivančić, V.; Mastali, M.; Percy, N.; Gornbein, J.; Babbitt, J. T.; Li, Y.; Landaw, E. M.; Bruckner, D. a.; Churchill, B. M.; Haake, D. a. Rapid Antimicrobial Susceptibility Determination of Uropathogens in Clinical Urine Specimens by Use of ATP Bioluminescence. *J. Clin. Microbiol.* 2008, 46, 1213-1219.

(22) Besant, J. D.; Sargent, E. H.; Kelley, S. O. Rapid Electrochemical Phenotypic Profiling of Antibiotic-Resistant Bacteria. *Lab Chip* 2015, 15, 2799-2807.

(23) Ertl, P.; Robello, E.; Battaglini, F.; Mikkelsen, S. R. Rapid Antibiotic Susceptibility Testing via Electrochemical Measurement of Ferricyanide Reduction by *Escherichia Coli* and *Clostridium Sporogenes*. *Anal. Chem.* 2000, 72, 4957-4964.

(24) Mann, T. S.; Mikkelsen, S. R. Antibiotic Susceptibility Testing at a Screen-Printed Carbon Electrode Array. *Anal. Chem.* 2008, 80, 843-848.

(25) Longo, G.; Alonso-Sarduy, L.; Rio, L. M.; Bizzini, a; Trampuz, a; Notz, J.; Dietler, G.; Kasas, S. Rapid Detection of Bacterial Resistance to Antibiotics Using AFM Cantilevers as Nanomechanical Sensors. *Nat. Nanotechnol.* 2013, 8, 522-526.

(26) Syal, K.; Iriya, R.; Yang, Y.; Yu, H.; Wang, S.; Haydel, S. E.; Chen, H.-Y.; Tao, N. Antimicrobial Susceptibility Test with Plasmonic Imaging and Tracking of Single Bacterial Motions on Nanometer Scale. *ACS Nano* 2015, 10, 845-852.

(27) Lissandrello, C.; Inci, F.; Francom, M.; Paul, M. R.; Demirci, U.; Ekinci, K. L. Nanomechanical Motion of *Escherichia Coli* Adhered to a Surface. *Appl. Phys. Lett.* 2014, 113701, 113701-113704.

(28) von Ah, U.; Wirz, D.; Daniels, A. U. Isothermal Micro calorimetry—a New Method for MIC Determinations: Results for 12 Antibiotics and Reference Strains of *E. Coli* and *S. Aureus*. *BMC Microbiol.* 2009, 9, 106.

(29) Bonkat, G.; Braissant, O.; Widmer, A. F.; Frei, R.; Rieken, M.; Wyler, S.; Gasser, T. C.; Wirz, D.; Daniels, A. U.; Bachmann, A. Rapid Detection of Urinary Tract Pathogens Using Microcalorimetry: Principle, Technique and First Results. *BJU Int.* 2012,110, 892-897.

(30) Barczak, a. K.; Gomez, J. E.; Kaufmann, B. B.; Hinson, E. R.; Cosimi, L.; Borowsky, M. L.; Onderdonk, a. B.; Stanley, S. a.; Kaur, D.; Bryant, K. F.; et al. RNA Signatures Allow Rapid Identification of Pathogens and Antibiotic Susceptibilities. *Proc. Natl. Acad. Sci.* 2012, 109, 6217-6222.

(31) Berke, A. P.; Turner, L.; Berg, H. C.; Lauga, E. Hydrodynamic Attraction of Swimming Microorganisms by Surfaces. *Phys. Rev. Lett.* 2008, 101, 1-4.

(32) Molaei, M.; Barry, M.; Stocker, R.; Sheng, J. Failed Escape: Solid Surfaces Prevent Tumbling of *Escherichia Coli*. *Phys. Rev. Lett.* 2014, 113, 1-6.

(33) Frymier, P. D.; Ford, R. M.; Berg, H. C.; Cummings, P. T. Three-Dimensional Tracking of Motile Bacteria near a Solid Planar Surface. *Proc. Natl. Acad. Sci. U.S.A.* 1995, 92, 6195-6199.

(34) Sokolov, A.; Aranson, I. S. Reduction of Viscosity in Suspension of Swimming Bacteria. *Phys. Rev. Lett.* 2009, 103, 2-5.

(35) Aghayee, S.; Benadiba, C.; Notz, J.; Kasas, S.; Dietler, G.; Longo, G. Combination of Fluorescence Microscopy

(35) ... and Nanomotion Detection to Characterize Bacteria. *J. Mol. Recognit.* 2013, 26, 590-595.
(36) Syal, K.; Wang, W.; Shan, X.; Wang, S.; Chen, H. Y.; Tao, N. Plasmonic Imaging of Protein Interactions with Single Bacterial Cells. *Biosens. Bioelectron.* 2015, 63, 131-137.
(37) Besser, R. E.; Griffin, P. M.; Slutsker, L. *Escherichia Coli* O157:H7 Gastroenteritis and the Hemolytic Uremic Syndrome: An Emerging Infectious Disease. *Annu. Rev. Med.* 1999, 50, 355-367.
(38) Flores-Mireles, A. L.; Walker, J. N.; Caparon, M.; Hultgren, S. J. Urinary Tract Infections: Epidemiology, Mechanisms of Infection and Treatment Options. *Nat. Rev. Microbiol.* 2015, 13, 269-284.
(39) Kwa, A.; Kasiakou, S. K.; Tam, V. H.; Falagas, M. E. Polymyxin B: Similarities to and Differences from Colistin (Polymyxin E). *Expert Rev. Anti. Infect. Ther.* 2007, 5, 811-821.
(40) Lim, L. M.; Pharm, D.; Ly, N.; Anderson, D.; Pharm, D.; Yang, J. C.; Pharm, D.; Macander, L.; Pharm, D.; Hi, A. J.; et al. Resurgence of Colistin: A Review of Resistance, Toxicity, Pharmacodynamics, and Dosing. 2015, 30, 1279-1291.
(41) Mcgann, P.; Snesrud, E.; Maybank, R.; Corey, B.; Ong, A. C.; Clifford, R.; Hinkle, M.; Whitman, T. *Escherichia Coli* Harboring Mcr-1 and Bla CTX-M on a Novel IncF Plasmid: First Report of Mcr-1 in the United States. *Antimicrob Agents Chemother* 2016, 60, 4420-4421.
(42) Liu, Y.; Wang, Y.; Walsh, T. R.; Yi, L.; Zhang, R.; Spencer, J.; Doi, Y.; Tian, G.; Dong, B.; Huang, X.; et al. Emergence of Plasmid-Mediated Colistin Resistance Mechanism MCR-1 in Animals and Human Beings in China: A Microbiological and Molecular Biological Study. *Lancet Infect. Dis.* 2016, 16, 161-168.
(43) Subramanian, A.; lrudayaraj, J.; Ryan, T. A Mixed Self-Assembled Monolayer-Based Surface Plasmon Immunosensor for Detection of *E. Coli* O157:H7. *Biosens. Bioelectron.* 2006, 21, 998-1006.
(44) Liu, J.; Prindle, A.; Humphries, J.; Gabalda-sagarra, M.; Asally, M.; Lee, D. D. Metabolic Co-Dependence Gives Rise to Collective Oscillations within Biofilms. *Nature* 2015, 523, 550-554.
(45) Sochacki, K. a; Barns, K. J.; Bucki, R.; Weisshaar, J. C. Real-Time Attack on Single *Escherichia Coli* Cells by the Human Antimicrobial Peptide LL-37. *Proc. Natl. Acad. Sci. U.S.A.* 2011, 108, E77-81.
(46) Kearns, D. B. REVIEWS A Field Guide to Bacterial Swarming Motility. *Nat. Publ. Gr.* 2010, 8, 634-644.
(47) Bradford, P. A.; , Krystyna M Kazmierczak, Douglas J Biedenbach, Wise, M. G.; Hackel, M.; Sahm2, D. F. Colistin-Resistant Enterobacteriaceae: Correlation of β-Lactamase Production and Colistin Resistance among Isolates from a Global Surveillance Program. *Antimicrob Agents Chemother* 2015.
(48) Sheng, J.; Malkiel, E.; Katz, J. Digital Holographic Microscope for Measuring Three-Dimensional Particle Distributions and Motions. *Appl. Opt.* 2006, 45, 3893.
(49) Pitt, W. G.; Alizadeh, M.; Husseini, G. A.; Mcclellan, D. S.; Buchanan, C. M.; Bledsoe, C. G.; Robison, R. A.; Blanco, R.; Roeder, B. L.; Melville, M.; et al. Rapid Separation of Bacteria from Blood—Review and Outlook. *Biotechnol. Prog.* 2016, 32, 823-839.
(50) Wang, W.; Yang, Y.; Wang, S.; Nagaraj, V. J.; Liu, Q.; Wu, J.; Tao, N. Label-Free Measuring and Mapping of Binding Kinetics of Membrane Proteins in Single Living Cells. *Nat. Chem.* 2012, 4, 846-873.
(51) Wang, S.; Shan, X.; Patel, U.; Huang, X.; Lu, J.; Li, J.; Tao, N. Label-Free Imaging, Detection, and Mass Measurement of Single Viruses by Surface Plasmon Resonance. *Proc. Natl. Acad. Sci. U.S.A.* 2010, 107, 16028-16032.
(52) Shan, X.; Diez-Perez, I.; Wang, L.; Wiktor, P.; Gu, Y.; Zhang, L.; Wang, W.; Lu, J.; Wang, S.; Gong, Q.; et al. Imaging the Electrocatalytic Activity of Single Nanoparticles. *Nat. Nanotechnol.* 2012, 7, 668-672.
(53) Shen, S.; Syal, K.; Tao, N.; Wang, S. Note: An Automated Image Analysis Method for High-Throughput Classification of Surface-Bound Bacterial Cell Motions. *Rev. Sci. Instrum.* 2015, 86, 1-4.
(54) Wiegand, I.; Hilbert, K.; Hancock, R. E. W. Agar and Broth Dilution Methods to Determine the Minimal Inhibitory Concentration (MIC) of Antimicrobial Substances. *Nat. Protoc.* 2008, 3, 163-175.

What is claimed is:

1. A method for measuring the sub-micron motion of surface-tethered bacterial cells comprising:
adding different doses of at least one antibiotic to different ones of a plurality of wells in a multi-well glass slide, each well having a surface;
adding portions of a biological sample with live bacteria to the plurality of wells, incubating bacterial cells from the live bacteria tethering a plurality of bacterial cells onto one of the surfaces to create tethered bacterial cells;
operating a light microscopy apparatus to image each of the plurality of wells including imaging the tethered bacterial cells;
operating a camera to obtain images of the tethered bacterial cells from the light microscopy apparatus;
tracking the sub-micron motion of images of the tethered bacterial cells;
analyzing bacterial motion of tethered bacterial cells in different wells at the different doses;
operating a processor to apply an image analysis process to the images to quantitate the motions of the tethered bacterial cells so as to detect changes in the motions of the tethered bacterial cells;
storing the motion changes in a memory;
operating a processor to perform statistical analysis on a population of cells for each antibiotic dose to generate an antibiotic dose curve proportional to the motion changes; and
operating an imaging device and a processor for measuring the X and Y displacement of each tethered cell center by subtracting the X and Y coordinates of an individual cell from the cell's average position over the length of the image sequences and calculating a distance moved by the tethered cell center by using the formula
distance=$\sqrt{\sigma x^2 + \sigma y^2}$, where σx and σy represent the standard deviations of X and Y displacement, respectively.

2. The method of claim 1 wherein the surface is a glass surface further comprising treating the glass surface with linkers selected from the group consisting of APTES, antibodies, poly-l-lysine and tethering molecules.

3. The method of claim 1 wherein tethering bacterial cells comprises attaching tethering molecules to the surface, where the tethering molecules are selected from the group consisting of cell-adhesion promoting substances, poly-lysine, and agar matrix.

4. The method of claim 1 wherein the act of operating the processor to perform statistical analysis on the population of cells for each antibiotic dose to generate the antibiotic dose curve proportional to the motion changes further comprises:
- determining, using the imaging device and the processor, a distance range of bacterial cell motion;
- determining, using the processor, whether a distance range of bacterial cell motion is between 50 nm and 65 nm;
- determining, using the imaging device and the processor, a dose of antibiotic used to limit the distance range of bacterial cell motion between 50 nm and 65 nm; and
- reporting the dose as the minimum bactericidal concentration of antibiotic for the antibiotic.

5. The method of claim 1 further comprising operating a gravity-based multichannel drug perfusion system to deliver medium and buffers to the plurality of wells.

6. The method of claim 1 further comprising applying glass coverslips coated with chromium and to the multi-well glass slide as a sensor surface.

7. A method for rapid antibiotic susceptibility testing by tracking sub-micron scale motion of single bacterial cells comprising:
- adding different doses of at least one antibiotic to different ones of a plurality of wells in a multi-well glass slide, each well having a surface;
- adding portions of a biological sample with live bacteria to the plurality of wells, incubating bacterial cells from the live bacteria to tether a plurality of bacterial cells onto one of the surfaces to create tethered bacterial cells;
- operating a light microscopy apparatus to image each of the plurality of wells including imaging the tethered bacterial cells;
- operating a camera to obtain images of the tethered bacterial cells from the light microscopy apparatus;
- tracking the sub-micron scale motion of images of the tethered bacterial cells;
- analyzing bacterial motion of tethered bacterial cells in different wells at the different doses;
- operating a processor to apply an image analysis process to the images to quantitate the motions of the tethered bacterial cells to detect changes in the motions of the tethered bacterial cells;
- storing the motion changes in memory;
- operating a processor to perform statistical analysis on a population of cells for each antibiotic dose to generate an antibiotic dose curve proportional to the motion changes, wherein the antibiotic dose curve plots data including a decrease in movement over time indicating a proportional effectiveness of an antibiotic applied to a well; and
- operating an imaging device and a processor for measuring the X and Y displacement of each tethered cell center by subtracting the X and Y coordinates of an individual cell from the cell's average position over the length of the image sequences and calculating a distance moved by the tethered cell center by using the formula distance=$\sqrt{\sigma x^2 + \sigma y^2}$, where $\sigma x$ and $\sigma y$ represent the standard deviations of X and Y displacement, respectively.

8. The method of claim 7 further comprising creating the tethered bacterial cells by incubating the cells with APTES in Ethanol, incubated on the surface for up to 15 seconds.

9. The method of claim 7 wherein tethering the antibody comprises incubating 30 ug/ml of antibody solution for up to 30 mins on a PEG/PEG-COOH surface.

10. The method of claim 7 further comprising removing unattached bacterial cells prior to the act of operating the light microscopy apparatus to image each of the plurality of wells.

11. The method of claim 7 further comprising operating a gravity-based multichannel drug perfusion system to deliver medium and buffers to the plurality of wells.

12. The method of claim 7 further comprising applying glass coverslips coated with chromium and gold to the multi-well glass slide as a sensor surface.

13. A method for rapid antibiotic susceptibility testing by tracking sub-micron scale motion of single bacterial cells comprising:
- adding different doses of at least one antibiotic to different ones of a plurality of wells in a multi-well glass slide, each well having a surface;
- adding portions of a biological sample with live bacteria to the plurality of wells, incubating bacterial cells from the live bacteria to tether a plurality of bacterial cells onto one of the surfaces as tethered bacterial cells, where the tethered bacterial cells are incubated with APTES in Ethanol on the surface for up to 1 5 seconds;
- operating a light microscopy apparatus to image each of the plurality of wells including imaging the tethered bacterial cells;
- operating a camera to obtain images of the tethered bacterial cells from the light microscopy apparatus;
- tracking the sub-micron scale motion of images of the tethered bacterial cells;
- analyzing bacterial motion of tethered bacterial cells in different wells at the different doses;
- operating a processor to apply an image analysis process to the images to quantitate the motions of the tethered bacterial cells to detect changes in the motions of the tethered bacterial cells;
- storing the motion changes in a memory;
- operating a processor to perform statistical analysis on a population of cells for each antibiotic dose to generate an antibiotic dose curve proportional to the motion changes, wherein the antibiotic dose curve plots data including a decrease in movement over time indicating a proportional effectiveness of an antibiotic applied to a well; and
- operating an imaging device and a processor for measuring the X and Y displacement of each tethered cell center by subtracting the X and Y coordinates of an individual cell from the cell's average position over the length of the image sequences and calculating a distance moved by the tethered cell center by using the formula
distance=$\sqrt{\sigma x^2 + \sigma y^2}$, where $\sigma x$ and $\sigma y$ represent the standard deviations of X and Y displacement, respectively.

14. The method of claim 13 wherein tethering the antibody comprises incubating 36 ug/ml of antibody solution for up to 30 mins on a PEG/PEG-COOH surface.

15. The method of claim 13 further comprising removing unattached bacterial cells prior to the act of operating the light microscopy apparatus to image each of the plurality of wells.

16. The method of claim 13 further comprising operating a gravity-based multichannel drug perfusion method to deliver medium and buffers to the plurality of wells.

17. The method of claim 13 further comprising applying glass coverslips coated with chromium and gold to the multi-well glass slide as a sensor surface.

18. The method of claim 1 wherein the live bacteria are selected from the group consisting of *Escherichia coli* and uropathogenic *E. coli*.

19. The method of claim 7 wherein the live bacteria are selected from the group consisting of *Escherichia coli* and uropathogenic *E. coli*.

20. The method of claim 13 wherein the live bacteria are selected from the group consisting of *Escherichia coli* and uropathogenic *E. coli*.

* * * * *